US011850062B2

United States Patent
Adachi et al.

(10) Patent No.: US 11,850,062 B2
(45) Date of Patent: Dec. 26, 2023

(54) BIO-INFORMATION MEASUREMENT DEVICE

(71) Applicant: OMRON HEALTHCARE CO., LTD., Muko (JP)

(72) Inventors: Yuma Adachi, Kyoto (JP); Chiaki Ebisu, Kyoto (JP)

(73) Assignee: OMRON HEALTHCARE CO., LTD., Muko (JP)

( * ) Notice: Subject to any disclaimer, the term of this patent is extended or adjusted under 35 U.S.C. 154(b) by 777 days.

(21) Appl. No.: 17/016,601

(22) Filed: Sep. 10, 2020

(65) Prior Publication Data

US 2020/0405220 A1 Dec. 31, 2020

Related U.S. Application Data

(63) Continuation of application No. PCT/JP2019/004607, filed on Feb. 8, 2019.

(30) Foreign Application Priority Data

Mar. 19, 2018 (JP) ................................. 2018-051457

(51) Int. Cl.
*A61B 5/02* (2006.01)
*A61B 5/00* (2006.01)
(Continued)

(52) U.S. Cl.
CPC .............. *A61B 5/48* (2013.01); *A44C 5/0007* (2013.01); *A61B 5/02141* (2013.01); *A61B 5/02225* (2013.01); *A44C 5/00* (2013.01)

(58) Field of Classification Search
CPC ....... A61B 5/681; A61B 5/48; A61B 5/02141; A61B 5/02225; A44C 5/0007; A44C 5/00; A44B 11/223
(Continued)

(56) References Cited

U.S. PATENT DOCUMENTS 5,689,859 A * 11/1997 Cuche ...................... A44C 5/24
24/69 J
5,829,104 A * 11/1998 Gay ......................... A44C 5/24
24/71 J
(Continued)

FOREIGN PATENT DOCUMENTS

CN 104739385 A 7/2015
CN 107635462 A 1/2018
(Continued)

OTHER PUBLICATIONS

Apr. 23, 2019 International Search Report issued in International Patent Application No. PCT/JP2019/004607.
(Continued)

*Primary Examiner* — Adam J Waggenspack
(74) *Attorney, Agent, or Firm* — Oliff PLC

(57) ABSTRACT

A biological information measuring device includes a buckle including a first plate having a plate shape and being fixed to the other end of a second plate frame member and a second plate having a plate shape being rotatable. The second plate has a part that extends beyond the first plate when the second plate overlaps an outer surface of the first plate. A first fixing element is on a side of the extended part that becomes an inner surface when the second plate overlaps the outer surface of the first plate. A second fixing element is engageable with the first fixing element on the outer surface of the front end of the belt. An first engagement protrusion is on the first plate, and a second engagement protrusion overlaps the first engagement protrusion in a direction with the first engagement protrusion is on the second plate.

7 Claims, 15 Drawing Sheets

(51) Int. Cl.
   *A44C 5/00*   (2006.01)
   *A61B 5/021*  (2006.01)
   *A61B 5/022*  (2006.01)

(58) Field of Classification Search
   USPC ..................................... 224/165; 24/265 WS
   See application file for complete search history.

(56) References Cited

U.S. PATENT DOCUMENTS

| | | | |
|---|---|---|---|
| 5,870,803 A | | 2/1999 | Jorst |
| 6,023,816 A | * | 2/2000 | Okada ..................... A44C 5/24 24/71 J |
| 6,457,216 B1 | * | 10/2002 | Lo ........................... A44C 5/24 24/71 J |

FOREIGN PATENT DOCUMENTS

| JP | 2006-115992 A | 5/2006 |
|---|---|---|
| JP | 2008-61842 A | 3/2008 |
| JP | 3145249 U | 10/2008 |
| JP | 2015-73826 A | 4/2015 |
| JP | 2015-226630 A | 12/2015 |
| JP | 2016-96955 A | 5/2016 |
| JP | 2017-121461 A | 7/2017 |
| JP | 6172341 B2 | 8/2017 |

OTHER PUBLICATIONS

Jan. 19, 2023 Office Action issued in Chinese Patent Application No. 201980016731.6.

\* cited by examiner

BIO-INFORMATION MEASUREMENT DEVICE

CROSS-REFERENCE TO RELATED APPLICATION

This is a continuation application of International Application No. PCT/JP2019/004607, with an International filing date of Feb. 8, 2019, which claims priority of Japanese Patent Application No. 2018-051457 filed on Mar. 19, 2018, the entire content of which is hereby incorporated by reference.

TECHNICAL FIELD

The present invention relates to a biological information measuring device, and more particularly, to a biological information measuring device attached to a rod-shaped portion to be measured such as a wrist.

BACKGROUND ART

Conventionally known as this kind of biological information measuring device is a biological information measuring device including a band-shaped belt to be wound around a portion to be measured, a body that is disposed at a base end part of the belt in a longitudinal direction and is provided with an element for measuring biological information, and a buckle for connecting the base end part and a front end part in the longitudinal direction of the belt so that the belt becomes annular, as disclosed, for example, in Patent Document 1 (Japanese Patent No. 6172341).

The buckle includes a first plate frame member mounted at one end part thereof on an inner surface side of the base end part of the belt so as to be rotatable about an axis intersecting the longitudinal direction of the belt. The first plate frame member extends in a plate shape from the one end part to the other end part on the opposite side. Furthermore, the buckle includes a second plate frame member mounted at one end part thereof on the other end part of the first plate frame member so as to be rotatable about an axis parallel to the aforementioned axis. The second plate frame member extends in a plate shape from the one end part to the other end part on the opposite side. The other end part of the second plate frame member is attachable to the front end part of the belt.

When using this biological information measuring device, a user attaches the other end part of the second plate frame member to the front end part of the belt to make the belt annular. In a state where the body and the first plate frame member and the second plate frame member of the buckle are open to each other, the user puts his or her hand through the ring of the belt, and then folds the body and the first plate frame member and the second plate frame member of the buckle onto each other. This allows the user to attach the biological information measuring device (including the belt and the body) onto the wrist.

SUMMARY OF THE INVENTION

When the user attaches the biological information measuring device to the wrist or removes the biological information measuring device from the wrist, that is, when the user puts his or her hand through the ring of the belt or pulls out the hand from the ring of the belt in a state where the body and the first plate frame member and the second plate frame member of the buckle are open to each other, the hand (first) is rubbed on the inner surface of the ring of the belt. As a result, the other end part of the second plate frame member is sometimes displaced from an adjusted position with respect to the front end part of the belt in a direction in which the ring of the belt expands. According to this biological information measuring device, the user may therefore become unable to find the original attachment position (adjusted position).

An object of this invention is to provide a biological information measuring device of this type provided with a buckle that is improved in position adjustment between the other end part of the second plate frame member and the front end part of the belt.

In order to solve the above-mentioned problem, a biological information measuring device of the present disclosure wound around a rod-shaped portion to be measured, comprises:
  a band-shaped belt that is wound around the portion to be measured;
  a body that is disposed on a base end part of the belt in a longitudinal direction and is provided with an element for measuring biological information; and
  a buckle that connects the base end part and a front end part on an opposite side in the longitudinal direction of the belt so that the belt becomes annular,
wherein
the buckle includes
  a first plate frame member that is attached at one end part thereof on an inner surface of the base end part of the belt so as to be rotatable about an axis that intersects the longitudinal direction of the belt, the first plate frame member extending in a plate shape from the one end part to an other end part on an opposite side,
  a second plate frame member that is attached at one end part thereof to the other end part of the first plate frame member so as to be rotatable about an axis parallel with the axis, the second plate frame member extending in a plate shape from the one end part to an other end part on an opposite side, and the other end part of the second plate frame member being attachable to the front end part of the belt, and
  a first plate part having a plate shape and being fixed to the other end part of the second plate frame member so as to be integral with the second plate frame member and a second plate part having a plate shape and attached so as to be rotatable about a rotation axis parallel with the axis and located at a forefront end of the other end part,
the second plate part has a sticking-out part that extends beyond the first plate part toward the one end part of the second plate frame member when the second plate member overlaps an outer surface of the first plate part,
a first fixing element is provided on a side of the sticking-out part that becomes an inner surface when the second plate part overlaps the outer surface of the first plate part, and a second fixing element that is engageable with the first fixing element is provided on an outer surface of the front end part of the belt, and
a first engagement protrusion is provided on a specific part of an end side of the first plate part closer to the one end part of the second plate frame member, and a second engagement protrusion that overlaps the first engagement protrusion in a thickness direction and is engageable with the first engagement protrusion is provided in a part of the second plate part that corresponds to the first engagement protrusion.

In the present specification, a "base end part", a "front end part", a "one end part" and an "other end part" are not limited to a base end, a front end, one end, and the other end, respectively, and may refer to a part in a certain range. Meanwhile, a "foremost end" substantially refers to a front end.

An "inner surface" refers to a surface that faces a portion to be measured in a state where the biological information measuring device is wound around the portion to be measured. An "outer surface" refers to a surface opposite to the inner surface in a state where the biological information measuring device is wound around the portion to be measured.

"Biological information" broadly encompasses a blood pressure value, a pulse value, an activity amount, a blood oxygen concentration value, and the like.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF EMBODIMENTS

Hereinafter, an embodiment of the present invention will be described in detail with reference to the drawings.

(Overall Configuration of Device)

Figure 1A:
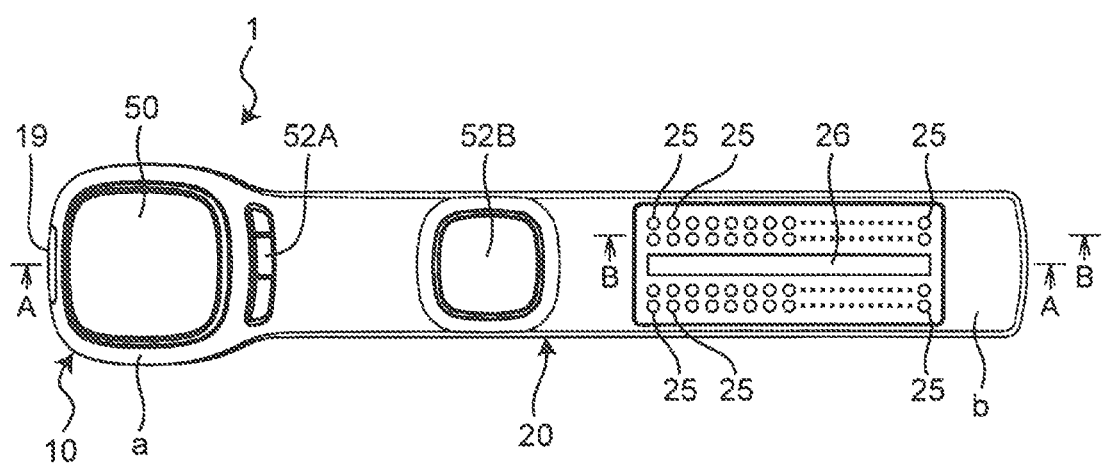
FIG. 1A is a top view showing an appearance of an unfolded state of a biological information measuring device according to an embodiment of the present invention.
Figure 1B:
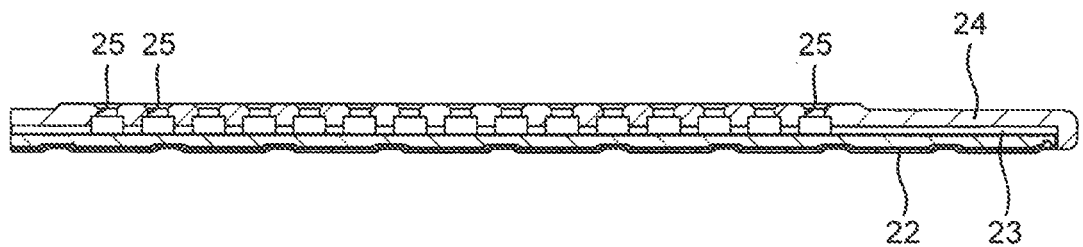
FIG. 1B is a vertical cross-sectional view of the biological information measuring device taken along line B-B in FIG. 1A.
Figure 1C:
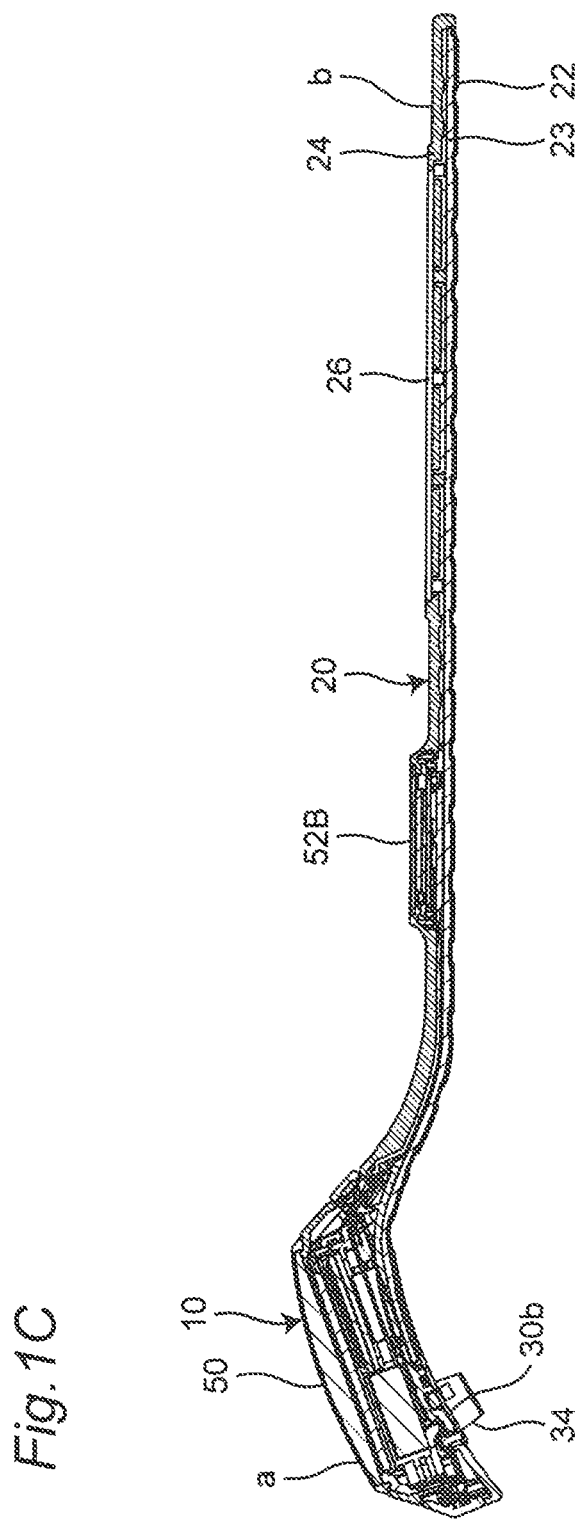
FIG. 1C is a vertical cross-sectional view of the biological information measuring device taken along line A-A in FIG. 1A.
Figure 1D:
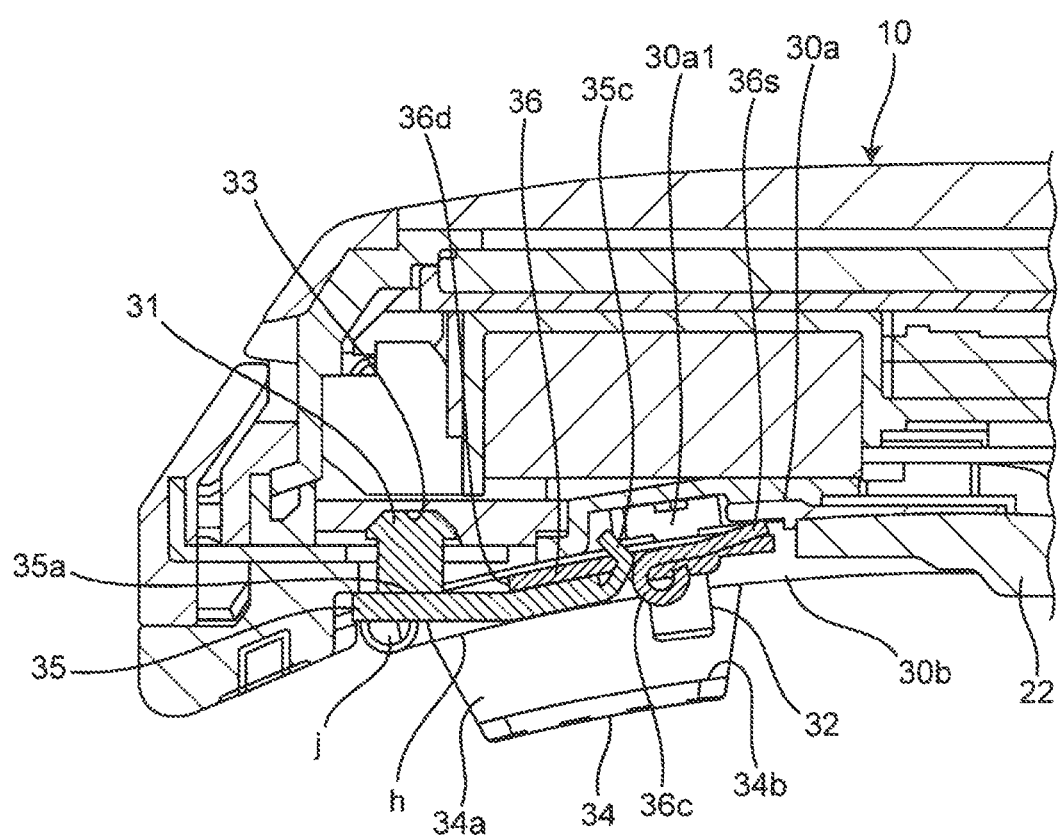
FIG. 1D is an enlarged view showing a part of the body of the biological information measuring device in FIG. 1C.
Figure 2:
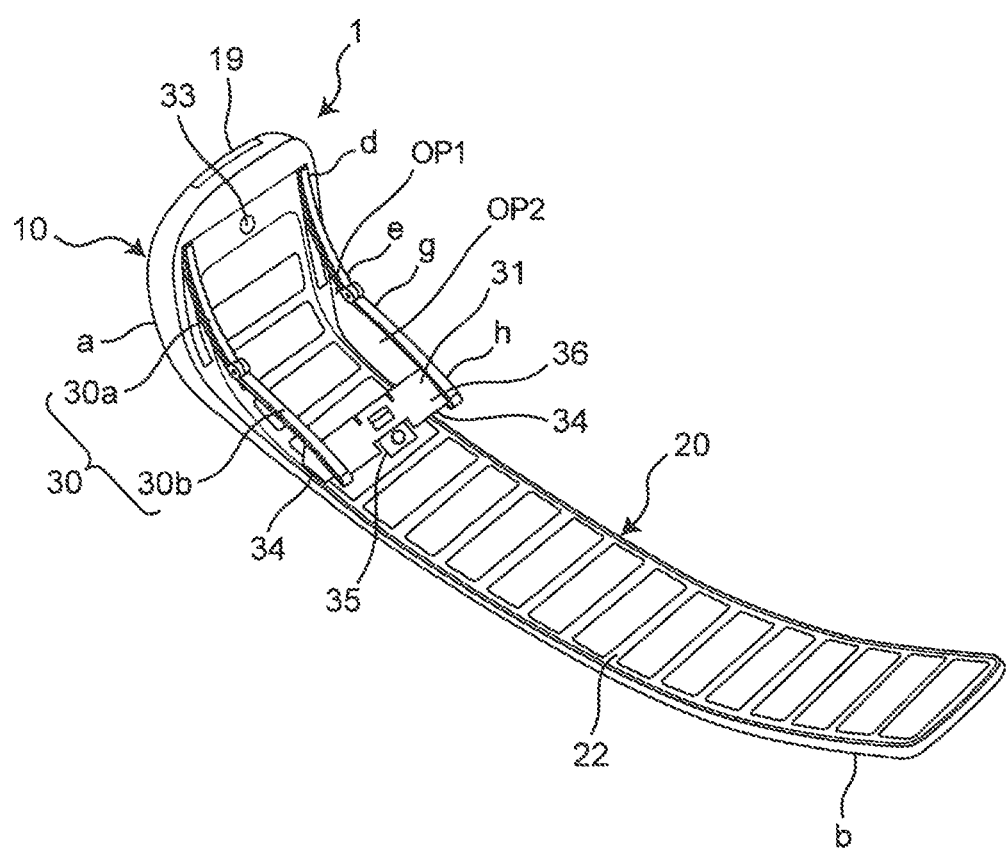
FIG. 2 is a bottom view of the biological information measuring device.
Figure 3:
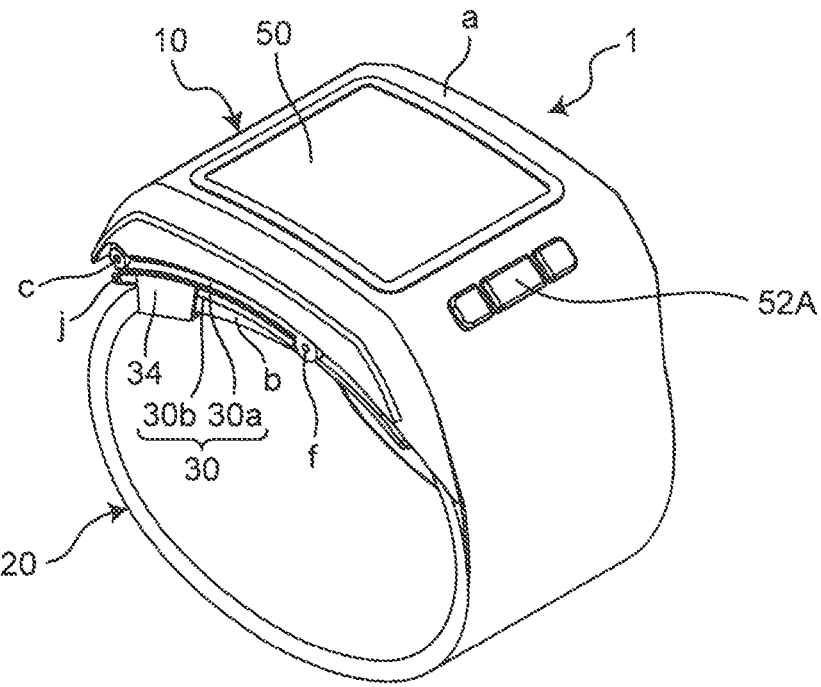
FIG. 3 is a perspective view showing a state where the biological information measuring device is made annular.
Figure 4:
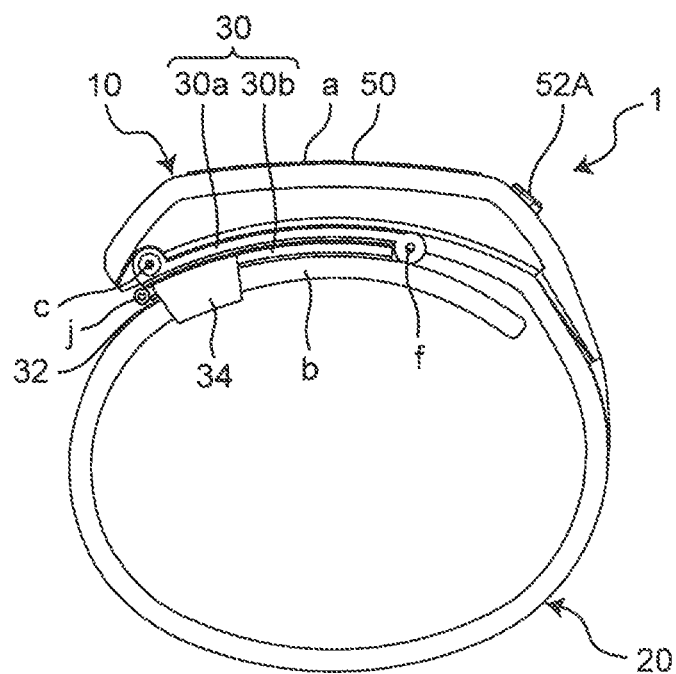
FIG. 4 is a view showing the biological information measuring device of FIG. 3 viewed from a direction (side) perpendicular to the ring of the belt.

FIG. 1A is a top view showing an appearance of an unfolded state of a biological information measuring device 1 according to an embodiment of the present invention, FIG. 1B is a vertical cross-sectional view of the biological information measuring device 1 taken along line B-B in FIG. 1A, and FIG. 1C is a vertical cross-sectional view of the biological information measuring device 1 taken along line A-A in FIG. 1A. FIG. 1D is an enlarged cross-sectional view showing a part of a body 10 of the biological information measuring device 1 of FIG. 1C. FIG. 2 is a bottom view of the biological information measuring device 1 of FIG. 1. FIG. 3 is a perspective view showing a state where the biological information measuring device 1 of FIG. 1 is made annular, and FIG. 4 shows the biological information measuring device 1 of FIG. 3 viewed from a direction (side) perpendicular to the ring of a belt 20. The biological information measuring device 1 is a device that is wound around a rod-shaped portion to be measured such as a user's wrist 90 (see FIGS. 8F to 8H) to measure blood pressure and other kinds of biological information.

As shown in FIG. 3 and FIG. 4, the biological information measuring device 1 includes the band-shaped belt 20 wound around a portion to be measured, a body 10 that is disposed on a base end part a in a longitudinal direction of the belt 20 and is provided with an element for measuring blood pressure, and a buckle 30 for connecting the base end part a and a front end part b on an opposite side in the longitudinal direction of the belt 20 so that the belt 20 becomes annular. In this example, the belt 20 serves as a blood pressure measurement cuff. The body 10 is equipped with a display device 50 and a power switch 52A that is a part of an operation unit 52.

(Configuration of Belt)

As shown in FIG. 2, a fluid bag 22 is provided on an inner surface side of the belt 20 along the longitudinal direction of the belt 20 to press the portion to be measured during blood pressure measurement. As shown in FIG. 1B, the belt 20 includes the fluid bag 22, a reinforcing layer 23 that is provided along an outer surface of the fluid bag 22 to suppress outward expansion of the fluid bag 22, and an outer peripheral layer 24 that is provided along an outer surface of the reinforcing layer 23 and covers the reinforcing layer 23. Therefore, since outward expansion of the fluid bag 22 can be suppressed, it is possible to improve efficiency of pressing the portion to be measured and further improve blood pressure measurement accuracy. A surface (which becomes an inner surface in an attached state) of the fluid bag 22 has a plurality of irregularities along the longitudinal direction so as to be easily expanded toward the portion to be measured.

The fluid bag 22, the reinforcing layer 23, and the outer peripheral layer 24 that constitute the belt 20 are each formed of an elastomer material. Therefore, the belt 20 has flexibility and therefore can be wound around the wrist 90. Furthermore, the belt is less likely to become dirty and can be wiped with water.

Furthermore, the reinforcing layer 23, the outer peripheral layer 24, and the fluid bag 22 decrease in hardness in this order. Therefore, when the fluid bag 22 expands, the reinforcement layer 23 can suppress outward expansion of the fluid bag 22, and thus efficiency of pressing the portion to be measured can be improved. This can further improve blood pressure measurement accuracy. Furthermore, since the outer periphery of the reinforcement layer 23 is covered with the outer periphery layer 24 having a hardness smaller than the hardness of the reinforcement layer 23, the user who touches the outer periphery layer 24 of the belt 20 feels soft.

Figure 5:
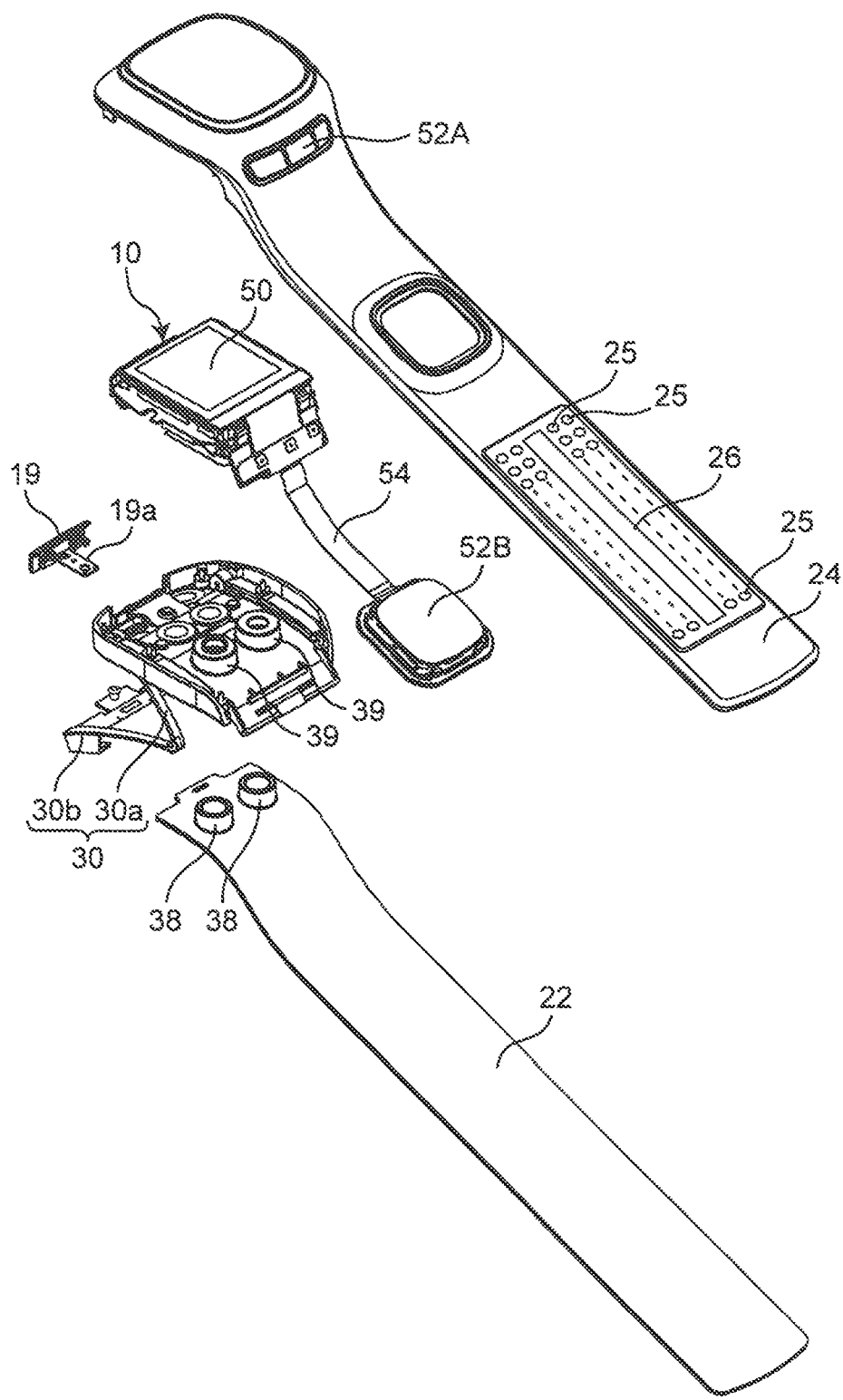
FIG. 5 is an exploded perspective view for explaining a structure of the biological information measuring device.

As shown in FIG. 1A and FIG. 1C, a blood pressure measurement switch 52B for receiving an instruction to measure biological information, which is a part of the operation unit, is disposed in a portion (substantially central portion in this example) different from the base end part a where the body 10 is disposed in the longitudinal direction of the belt 20. Furthermore, as shown in FIG. 5 (exploded view), an FPC cable 54 that electrically connects the body 10 and the blood pressure measurement switch 52B is interposed between the fluid bag 22 and the reinforcing layer 23. Since the body 10 and the blood pressure measurement switch 52B are electrically connected by the FPC cable 54, the belt 20 can be made thin. Although only the operation unit (in this example, the blood pressure measurement switch 52B) is disposed in the substantially central part in the longitudinal direction of the belt 20 in the present embodiment, the present invention is not limited to this, and a communication unit and a display unit may also be disposed.

As shown in FIG. 1A, FIG. 1B, and FIG. 5, a groove 26 having a concave cross section is provided on the outer surface of the front end part b of the belt 20 in a central part in a width direction of the belt 20 so as to extend along the longitudinal direction. On a bottom of the groove 26, marks M representing numbers 1 to 10 for adjusting the position of the front end part b of the belt 20 are provided (see FIGS. 8A to 8E, which will be described later). On the outer surface of the front end part b of the belt 20, a plurality of engaged parts 25 having a concave shape are provided as a second fixing element in portions corresponding to both sides of the groove 26 in the width direction. In this example, two engaged parts 25 are arranged on each side of the groove 26, four engaged parts 25 in total, in the width direction. A plurality of combinations (a large number of combinations in this example) of these four engaged parts 25 are arranged side by side along the longitudinal direction of the belt 20. This makes it possible to adjust an attachment position of the other end part h of a second plate frame member 30b in the longitudinal direction of the belt 20. Furthermore, as shown in FIG. 2, a magnet 33, which is a second lock element, is provided on the inner surface side of the base end part a of the belt 20 (or on a one end part d of a first plate frame member 30a (will be described later) that constitutes the buckle 30). Operation of these elements will be described later.

(Configuration and Function of Buckle)

Figure 6A:
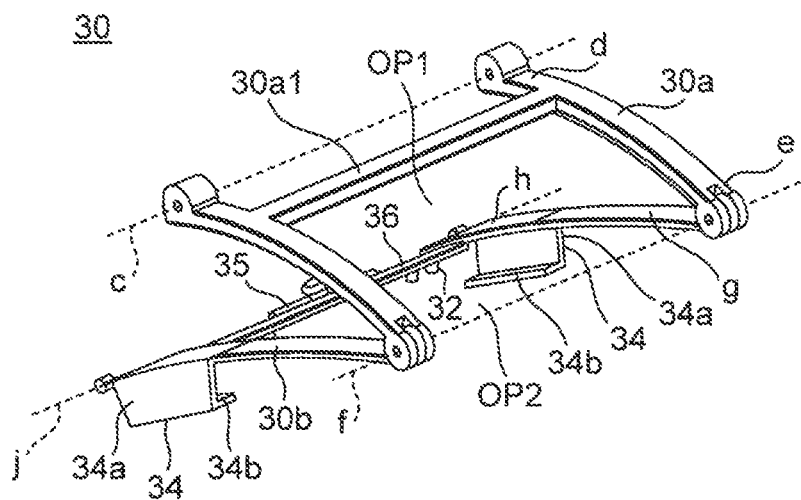
FIG. 6A is a perspective view showing a configuration of a buckle that constitutes the biological information measuring device.
Figure 6B:
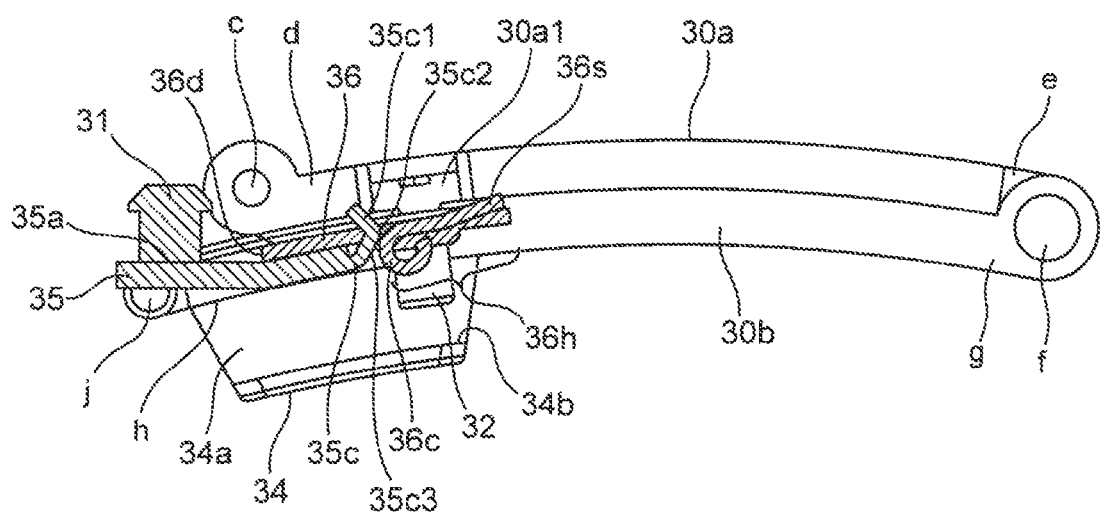
FIG. 6B is a side view showing the buckle in a folded state.
Figure 6C:
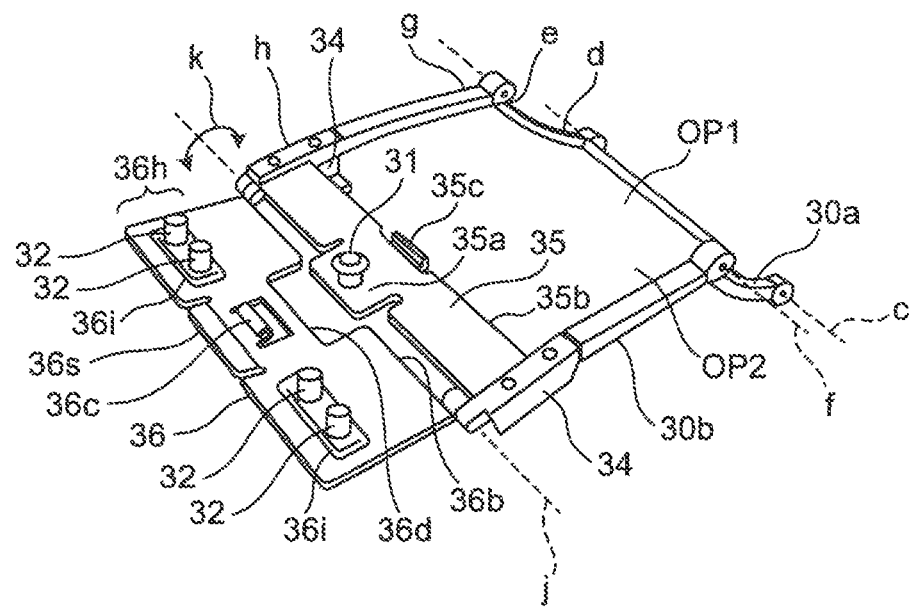
FIG. 6C is a perspective view showing a state in which a first plate frame member and a second plate frame member that constitute the buckle are opened and a second plate part is opened with respect to a first plate part that constitutes the buckle.

FIGS. 6A to 6C show a configuration of the buckle 30. FIG. 6A corresponds to a state in which the buckle 30 is opened by about 30°, FIG. 6B corresponds to a state in which the buckle 30 is closed, and FIG. 6C corresponds to a state in which the buckle 30 is opened by more than 180°.

In this example, the buckle 30 includes the first plate frame member 30a that is attached at one end part d on the inner surface side of the base end part a of the belt 20 so as to be rotatable about an axis c that intersects the longitudinal direction of the belt 20. The first plate frame member 30a extends so as to be curved in a plate shape from the one end part d to the other end part e on the opposite side. The first plate frame member 30a has a beam part 30a1 extending in the width direction near the one end part d. The beam part 30a1 can increase the rigidity of the buckle 30 (the first plate frame member 30a). Furthermore, the buckle 30 includes the second plate frame member 30b attached to the other end part e of the first plate frame member 30a so as to be rotatable about an axis f parallel to the axis c. The second plate frame member 30b extends so as to be curved in a plate shape from a one end part g to the other end part h on the opposite side. As will be described later, the other end part h of the second plate frame member 30b is configured to be attachable to the front end part b of the belt 20.

The first plate frame member 30a and the second plate frame member 30b have a first opening OP1 and a second opening OP2, respectively, that pass through the respective members with respect to plate surfaces thereof. In a state where the inner surface of the body 10 and the first plate frame member 30a and the second plate frame member 30b of the buckle 30 are folded so as to overlap one another, the first opening OP1 of the first plate frame member 30a and the second opening OP2 of the second plate frame member 30b are continuous with each other in a thickness direction of the body 10.

This can achieve a configuration in which the fluid bag 22 is disposed on the inner side of the body 10 so as to press the portion to be measured.

The first opening OP1 is opened toward the other end part e of the first plate frame member 30a and the second opening OP2 is opened toward the one end part g of the second plate frame member 30b, so that the first opening OP1 and the second opening OP2 are communicated with each other. That is, the first plate frame member 30a and the second plate frame member 30b are each formed in a substantially U shape and are connected to each other on the sides where the openings are opened. The fluid bag 22 described above communicates with the inside of the body 10 through a region corresponding to the first opening OP1 and the second opening OP2 in a state where the buckle 30 is folded.

With this configuration, a region of the wrist 90 to be measured that is spatially continuous from a portion corresponding to the inner side of the body 10 toward the front end part b of the belt 20 in the circumferential direction can be pressed by the fluid bag 22. This can increase a contact area between the fluid bag 22 and the portion to be measured, thereby improving efficiency of pressing an artery. This can further improve blood pressure measurement accuracy.

As shown in FIGS. 1B, 1C and 2, the fluid bag 22 extends along the longitudinal direction to the front end part b of the belt 20. Then, in a state where the inner surface of the main body 10 and the first plate frame member 30a and the second plate frame member 30b of the buckle 30 are folded so as to overlap each other, a portion of the body 10 with which the fluid bag 22 is communicated overlaps a portion where the fluid bag 22 of the belt 20 extends.

With this configuration, the overlapping region of the belt 20 in the longitudinal direction expands by a thickness larger than a thickness of the other regions of the body 10. Therefore, a distance over which an artery of the wrist 90 escapes by being pressed by a region other than the overlapping region is shortened. This saves unnecessary pressing for crushing the artery. As a result, a blood pressure measurement value measured by pressing by the fluid bag approaches a true value. That is, measurement accuracy can be improved. Note that the effect of reducing unnecessary pressing for crushing the artery is also obtained in a case where the first opening OP1 of the first plate frame member 30a and the second opening OP2 of the second plate frame member 30b are omitted in the buckle 30.

As shown in FIG. 6C, the buckle 30 includes a first plate part 35 having a plate shape and being integrally fixed to the second plate frame member 30b so as to extend in the width direction at the other end part h of the second plate frame member 30b and a second plate part 36 having a plate shape and provided so as to be rotatable as indicated by arrow k about a rotation axis j that is parallel to the axes c and f and is located at the foremost end of the other end part h.

The first plate part 35 has, in a central part thereof in the width direction, an island part 35a that slightly protrudes in a direction in which the second plate frame member 30b extends. A protrusion 31 made of a metal, which serves as a first lock element, is provided on a part of an outer surface of the island part 35a that corresponds to the foremost end of the other end part h (in this example, on a part corresponding to the magnet 33 serving as the second lock element shown in FIG. 2 in a state where the buckle 30 is folded). Furthermore, as shown in FIG. 6C, a first engagement protrusion 35c protruding upward (in FIGS. 6B and 6C) in a thickness direction in an L-shaped cross section (see FIG. 6B) is provided in a central portion (specific part) of an end side 35b closer to the one end part g of the first plate part 35.

As shown in FIG. 6C, the second plate part 36 has a sticking-out part 36h that extends beyond the first plate part 35 toward the one end part g when the second plate part 36 overlaps the outer surface of the first plate part 35. On a side of the sticking-out part 36h that becomes an inner surface when the second plate part 36 overlaps the outer surface of the first plate part 35, engaging parts 32 having a convex shape are provided as a first fixing element. In this example, two engaging parts 32 are arranged on both sides in the width direction (four engaging parts 32 in total) so as to correspond to the engaged parts 25 (for example, see FIG. 1A) provided on the outer surface of the front end part b of the belt 20 in the width direction. In this example, two regions 36i of the sticking-out part 36h on each of which two engaging parts 32 are provided are slightly raised upward (in FIG. 6C), for example, by pressing to increase strength of the plate material (these regions 36i are recessed on an opposite surface of the second plate part 36, as indicated by reference sign 36i' in FIG. 8A, for example). The four engaging parts 32 protrude downward (in FIGS. 6B and 1D) beyond the second plate frame member 30b as shown in FIG. 6B and FIG. 1D in a state where the second plate part 36 overlaps the outer surface of the first plate part 35. Accordingly, the four engaging parts 32 can be engaged with the four engaged parts 25 provided on the outer surface of the front end part b of the belt 20. This allows the second plate frame member 30b and the front end part b of the belt 20 to be engaged with each other to make the belt 20 annular, as shown in FIGS. 3 and 4. A dimension by which the engaging parts 32 protrudes downward in the state in which the second plate part 36 overlaps the outer surface of the first plate part 35 is set so that the engaging parts 32 make contact with and press bottoms of the engaged parts 25 having a concave shape.

As shown in FIG. 6C, the second plate part 36 has, in this example, a cutout (or an opening) 36d in a part thereof corresponding to the protrusion 31 when the second plate part 36 overlaps the outer surface of the first plate part 35. This can prevent the second plate part 36 from interfering with the protrusion 31 when the second plate part 36 is rotated about the rotation axis j and overlaps the outer surface of the first plate part 35. As a result, the protrusion 31 serving as the first lock element and the magnet 33 serving as the second lock element can stick to each other and/or be engaged with each other through the cutout 36d of the second plate part 36 in the state where the inner surface of the body 10 and the first plate frame member 30a and the second plate frame member 30b of the buckle 30 are folded so as to overlap each other, as described later.

Furthermore, an operation protrusion 36s for rotating the second plate part 36 about the rotation axis j is provided in a central part of the end side 36a that constitutes a foremost end of the sticking-out part 36h of the second plate part 36. In this example, the operation protrusion 36s protrudes so as to be bent toward an outer surface side of the second plate part 36. This allows a user to easily rotate the second plate part 36 about the rotation axis by hooking his or her finger on the operation protrusion 36s of the second plate part 36.

Furthermore, as shown in FIG. 6C, a second engagement protrusion 36c (see FIG. 6B) that protrudes upward (downward in FIG. 6B) in the thickness direction in an arc shape in cross-sectional view is provided in a part of the second plate part 36 that corresponds to the first engagement protrusion 35c. Accordingly, when the second plate part 36 is rotated about the rotation axis j and overlaps the outer surface of the first plate part 35, the second engagement protrusion 36c and the first engagement protrusion 35c overlap in the thickness direction and can be engaged with each other. Specifically, when the second plate part 36 is rotated about the rotation axis j and overlaps the outer surface of the first plate part 35, first, the "arc" of the second engagement protrusion 36c shown in FIG. 6B makes contact with an upper half 35c1 of the "L shape" of the first engagement protrusion 35c. Furthermore, when the second plate part 36 is further rotated downward (in FIG. 6B) about the rotation axis j, the "arc" of the second engagement protrusion 36c moves beyond an apex 35c2 of the "L shape" of the first engagement protrusion 35c and comes into contact with a lower half 35c3 of the "L shape". As a result, the second engagement protrusion 36c and the first engagement protrusion 35c overlap and engage with each other in the thickness direction. In this engaged state, the second plate part 36 does not open carelessly with respect to the first plate part 35. Therefore, in the state where the second plate part 36 overlaps the outer surface of the first plate part 35, the state in which the four engaging parts 32 protrude below the second plate frame member 30b is maintained.

Furthermore, even in a case where force is applied to the second plate part 36 from the first plate frame member 30a side when the first plate frame member 30a and the second plate frame member 30b of the buckle 30 are folded to overlap each other in the state where the second plate part 36 overlaps the outer surface of the first plate part 35, the force causes the second plate part 36 to rotate downward, that is, in the direction in which the second plate part 36 is pressed against the front end part b of the belt 20. Accordingly, when the buckle 30 is folded, the second plate part 36 does not open carelessly with respect to the first plate part 35. Furthermore, in a case where force is applied to the second plate part 36 between the body 10 and the belt 20 as a result of pressing of the fluid bag 22 of the belt 20 during the blood pressure measurement described later, the force causes the second plate part 36 to rotate in a direction in which the second plate part 36 is pressed against the front end part b of the belt 20. Accordingly, when the fluid bag 22 of the belt 20 is pressed, the second plate part 36 does not open carelessly with respect to the first plate part 35. If the direction of rotation of the second plate part 36 is opposite to that in this example, the second plate part 36 may be carelessly opened with respect to the first plate part 35 during buckle fastening or pressing.

As shown in FIG. 6B, the second engagement protrusion 36c of the second plate part 36 protrudes downward in the thickness direction, that is, toward a side where the front end part b of the belt 20 is arranged. Accordingly, as shown in FIG. 1D, the second engagement protrusion 36c, together with the beam part 30a1 of the first plate frame member 30a, can avoid interference with the body 10 side. As described above, the groove 26 having a concave cross section is provided in a central part (i.e., a part corresponding to the first engagement protrusion 35c and the second engagement protrusion 36c) in the width direction on the outer surface of the front end part b of the belt 20 so as to extend along the longitudinal direction. Accordingly, this groove 26 having a concave cross section can avoid interference between the outer surface of the belt 20 and the first engagement protrusion 35c and the second engagement protrusion 36c. As a result, the thickness of a part of the biological information measuring device 1 where the body 10, the buckle 30, and the belt 20 overlap can be reduced as a whole.

Furthermore, the groove 26 having a concave cross section widens a gap in the thickness direction between the operation protrusion 36s of the second plate part 36 and the outer surface of the front end part b of the belt 20 in the state in which the second plate part 36 overlaps the outer surface of the first plate part 35. This allows the user to easily hook his or her finger on the operation protrusion 36s of the second plate part 36.

Although the first engagement protrusion 35c and the second engagement protrusion 36c are disposed in the central parts (specific parts), in the width direction, of the first plate part 35 and the second plate part 36, respectively, and the groove 26 having a concave cross section is disposed in the central part, in the width direction, of the outer surface of the belt 20 accordingly in this example, this configuration is not restrictive. These elements may be arranged in pairs in parts other than the central part in the width direction, for example, between the central part and one edge and between the central part and the other edge.

Furthermore, as shown in FIG. 6A, a pair of hook parts 34 having an L-shaped cross section are provided on respective sides in the width direction of the other end part h of the second plate frame member 30b. Each hook part 34 has a side plate part 34a extending vertically downward (in FIG. 6A) in a plate shape with respect to the second plate frame member 30b and a front end plate part 34b extending from a lower end of the side plate part 34a toward the central side in the width direction. A vertical dimension of each side plate part 34a is set to be slightly larger than a thickness dimension of the belt 20. A distance between the side plate parts 34a is set to be slightly larger than a width dimension of the belt 20. The hook parts 34 permit insertion of the front end part b of the belt 20 along the inner surface of the second plate frame member 30b and restrict separation of the front end part b of the belt 20 from the inner surface of the second plate frame member 30b. This allows the front end part b of the belt 20 to smoothly slide without being separated from the inner surface of the second plate frame member 30b when the user performs position adjustment between the other end part h of the second plate frame member 30b and the front end part b of the belt 20 by sliding the front end part b of the belt 20 in the longitudinal direction along the inner surface of the second plate frame member 30b in the state where the second plate part 36 is opened with respect to the first plate part 35.

(Attachment Procedure)

FIG. 8A to 8G show a procedure in which the user attaches the biological information measuring device 1 onto the wrist.

Figure 7A:
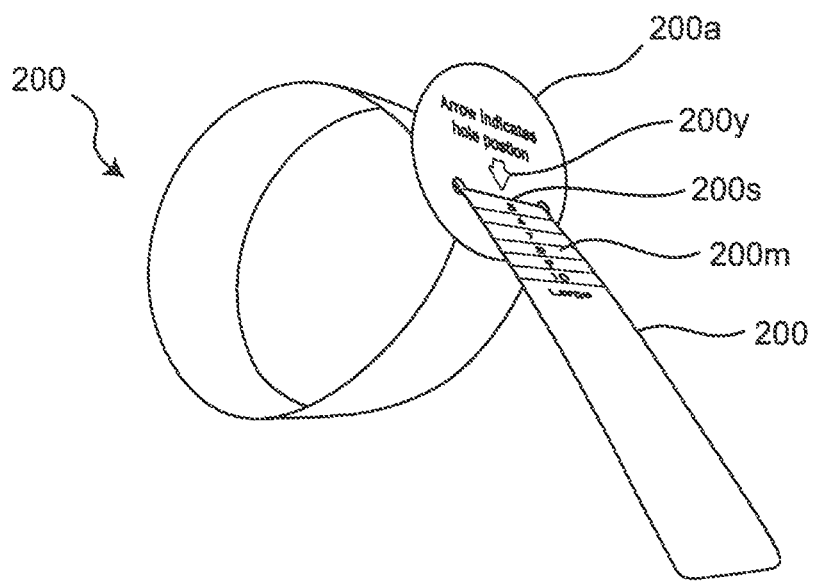
FIG. 7A is a diagram showing a configuration of a belt length guide member useful for attachment of the biological information measuring device.
Figure 7B:
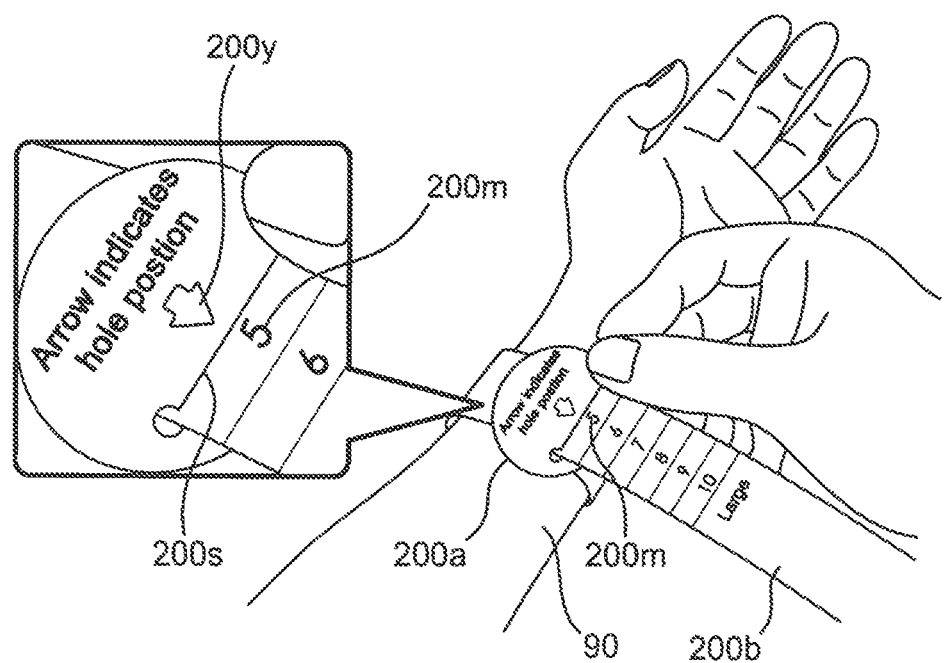
FIG. 7B is a diagram for explaining how to use the belt length guide member.

In this example, it is assumed that the user prepares a belt length guide member 200 as shown in FIG. 7A before the attachment. The belt length guide member 200 includes a circular head part 200a and a band part 200b that is an elongated part extending so as to be continuous with the head part 200a. The head part 200a has a slit 200s through which the band part 200b is passed to make the belt length guide member 200 annular. On an outer surface of the band part 200b, marks 200m representing numbers 1 to 10 are provided at positions corresponding to the marks M provided on the bottom of the groove 26 of the belt 20 described above. As shown in FIG. 7B, the user puts the wrist 90 through the ring of the belt length guide member 200, and adjusts the length of the ring of the belt length guide member 200 so that the length of the ring exactly matches the circumference of the wrist 90. The user checks and remembers a number (in this example, "5", which is indicated by an arrow 200y displayed on the head part 200a) of a mark 200m closest to the slit 200s.

(a) Position Adjustment Between the Other End Part h of the Second Plate Frame Member 30b and the Front End Part b of the Belt 20

Figure 8A:
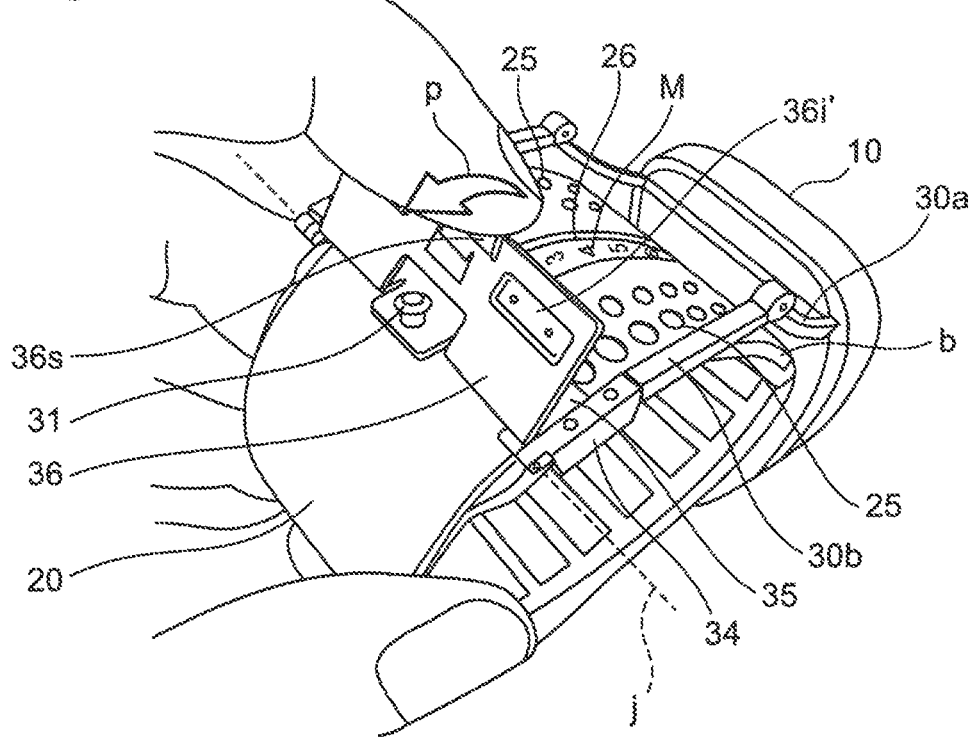
FIG. 8A is a diagram for explaining a procedure of attaching the biological information measuring device onto the wrist.
Figure 8B:
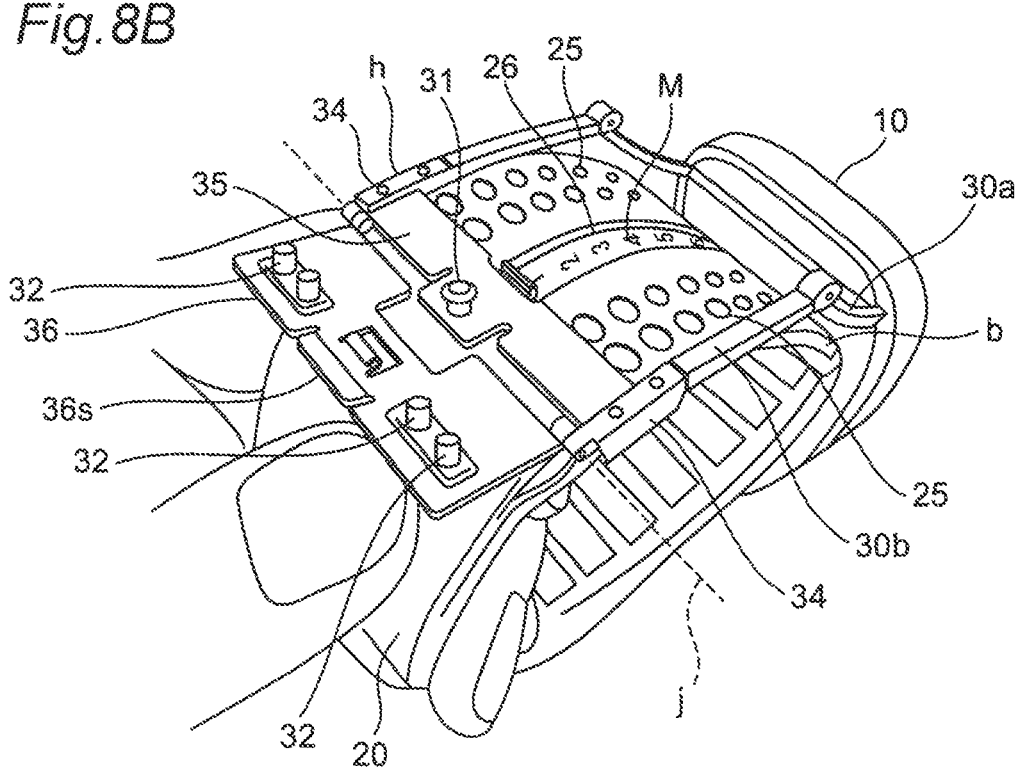
FIG. 8B is a diagram for explaining a procedure of attaching the biological information measuring device onto the wrist.
Figure 8C:
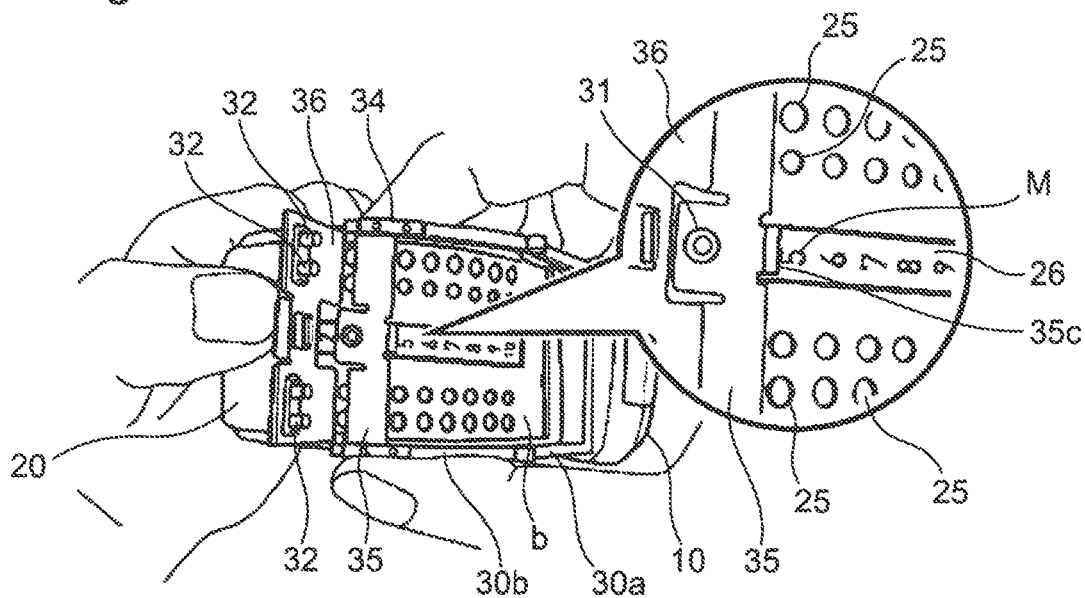
FIG. 8C is a diagram for explaining a procedure of attaching the biological information measuring device onto the wrist.

When attaching the biological information measuring device 1, the user hooks his or her finger on the operation protrusion 36s of the second plate part 36 to rotate the second plate part 36 about the rotation axis j as indicated by arrow p in a state where the body 10 and the first plate frame member 30a and the second plate frame member 30b of the buckle 30 are open to each other, as shown in FIGS. 8A and 8B. As a result, the second plate part 36 is brought into an opened state (non-overlapping state) with respect to the first plate part 35. At the same time, the user inserts the front end part b of the belt 20 between the pair of hook parts 34 of the second plate frame member 30b so that the front end part b of the belt 20 is arranged along the inner surface of the second plate frame member 30b. In this state, the other end part h of the second plate frame member 30b and the front end part b of the belt 20 are not fixed. Moreover, the hook parts 34 prevent the front end part b of the belt 20 from being separated from the inner surface of the second plate frame member 30b. This allows the user to slide the front end part b of the belt 20 in the longitudinal direction along the inner surface of the first plate part 35, thereby making it easy to perform position adjustment between the other end part h of the second plate frame member 30b and the front end part b of the belt 20. The user adjusts the position of the first engagement protrusion 35c of the first plate part 35 to an appropriate number (in this example, "5" found by the belt length guide member 200) among the marks M provided on the bottom of the groove 26 of the belt 20, as shown in FIG. 8C. Since the position adjustment is performed with reference to the marks M for position adjustment, the position adjustment can be performed accurately and with good reproducibility. In this way, the length of the ring of the belt 20 can be variably set so as to exactly match the circumference of the wrist 90.

(b) Attachment of the Other End Part h of the Second Plate Frame Member 30b and the Front End Part b of the Belt 20

Figure 8D:
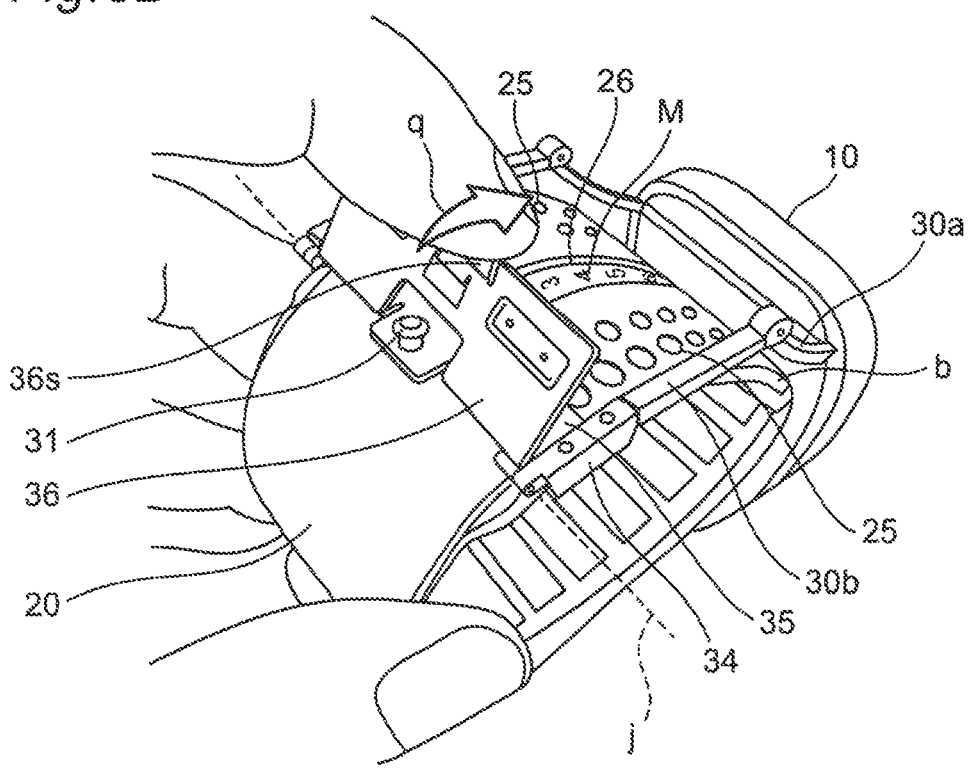
FIG. 8D is a diagram for explaining a procedure of attaching the biological information measuring device onto the wrist.
Figure 8E:
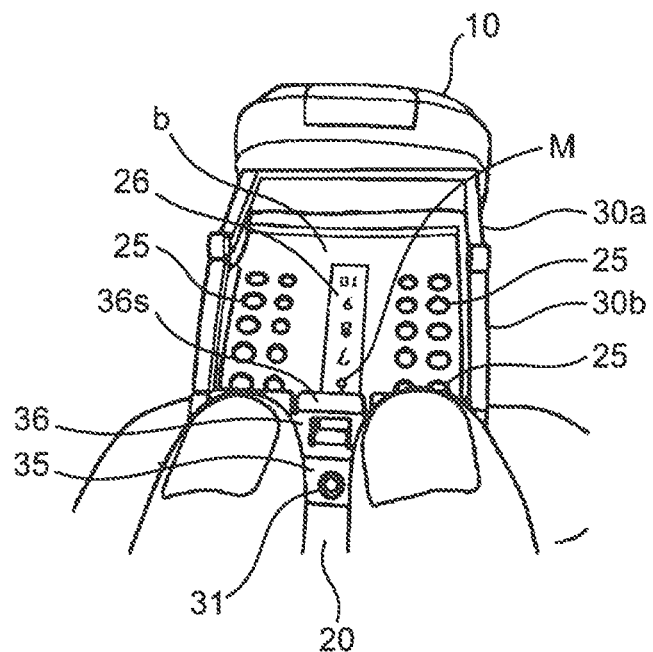
FIG. 8E is a diagram for explaining a procedure of attaching the biological information measuring device onto the wrist.

After finishing the position adjustment between the other end part h of the second plate frame member 30b and the front end part b of the belt 20, the user hooks his or her finger on the operation protrusion 36s of the second plate part 36 to rotate the second plate part 36 about the rotation axis j in a direction in which the second plate part 36 overlaps the outer surface of the first plate part 35 as indicated by arrow q, as shown in FIG. 8D. Furthermore, in this example, the user presses the second plate part 36 with both hands to close the second plate part 36 with respect to the first plate part 35, as shown in FIG. 8E. This causes the four engaging parts 32 serving as the first fixing element provided on the inner surface of the second plate part 36 to be engaged with corresponding (exactly matching) ones of the large number of engaged parts 25 serving as the second fixing element arranged along the longitudinal direction on the outer surface of the front end part b of the belt 20. As a result, the other end part h of the second plate frame member 30b is attached to the front end part b of the belt 20. In this state, the first engagement protrusion 35c of the first plate part 35 and the second engagement protrusion 36c of the second plate part 36 are engaged with each other in the thickness direction (see FIGS. 6B and 1D). This keeps the engagement between the other end part h of the second plate frame member 30b and the front end part b of the belt 20 while preventing the second plate part 36 from being opened carelessly with respect to the first plate part 35. This prevents the other end part h of the second plate frame member 30b and the front end part b of the belt 20 from being displaced from each other. In this state in which the second plate part 36 overlaps the outer surface of the first plate part 35, the engaging parts 32 provided on the inner surface of the second plate part 36 make contact with and press the bottoms of the engaged parts 25 provided on the outer surface of the front end part b of the belt 20, as described above. As a result, both edges of the belt 20 come into contact with and press the front end plate parts 34b of the hook parts 34 of the second plate frame member 30b. This eliminates gaps between both edges of the belt 20 and the front end plate parts 34b of the hook parts 34 of the second plate frame member 30b, thereby making the front end part b of the belt 20 less likely to be detached from the other end part h of the second plate frame member 30b.

(c) Folding of the Buckle 30

Figure 8F:
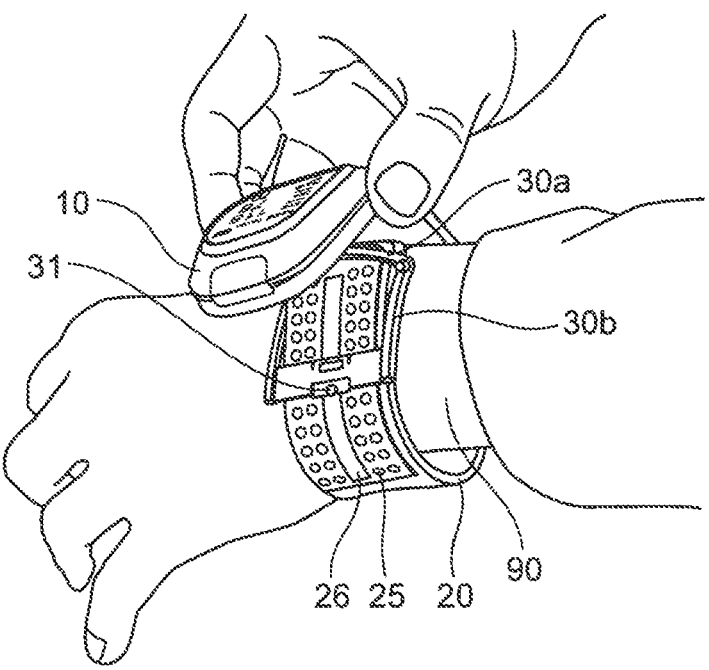
FIG. 8F is a diagram for explaining a procedure of attaching the biological information measuring device onto the wrist.
Figure 8G:
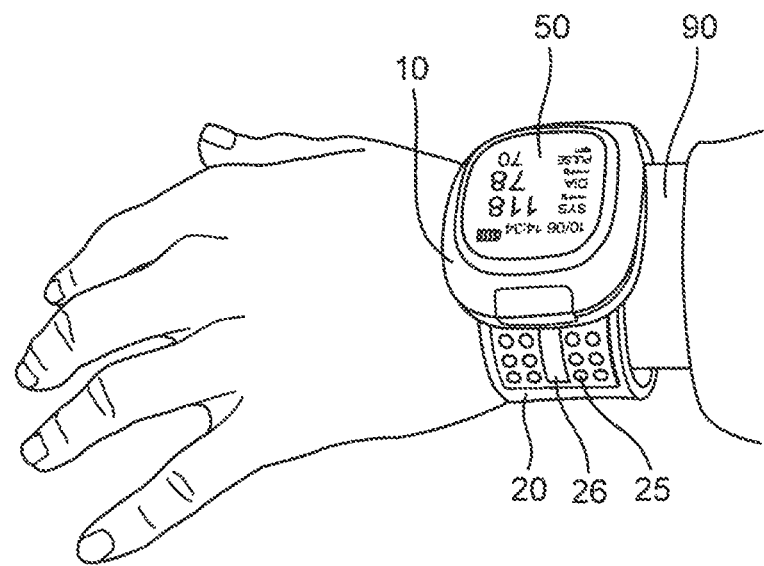
FIG. 8G is a diagram for explaining a procedure of attaching the biological information measuring device onto the wrist.

Then, as shown in FIG. 8F, the user puts his or her hand through the ring of the belt 20 in the state where the belt 20 is annular and the body 10 and the first plate frame member 30a and the second plate frame member 30b of the buckle 30 are opened to each other. Subsequently, the user folds the body 10 toward the wrist 90 side so that the inner surface of the body 10 and the first plate frame member 30a and the second plate frame member 30b of the buckle 30 overlap each other. This causes the protrusion 31 serving as the first lock element and the magnet 33 serving as the second lock element to stick to each other and/or be engaged with each other (see FIG. 1D) through the cutout 36d of the second plate part 36, as shown in FIG. 8G. This prevents the buckle 30 from being opened carelessly. In this way, the user can easily attach the biological information measuring device 1 onto the wrist (attached state).

In this example, a plurality of (four in this example) engaged parts 25 are arranged side by side along the width direction of the belt 20. Therefore, even if the belt 20 is slightly twisted, the engaging parts 32 and the engaged parts 25 are unlikely to be disengaged from each other.

Figure 8H:
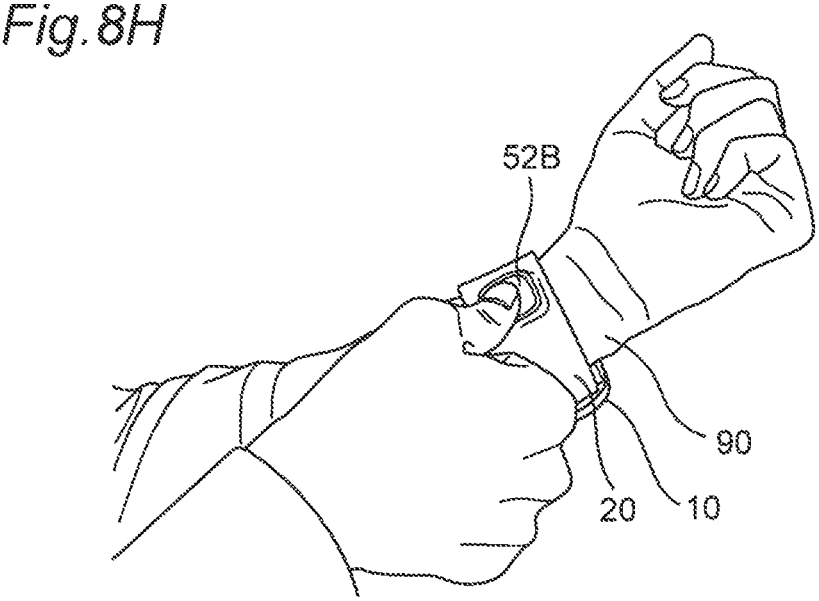
FIG. 8H is a diagram for explaining how a user gives an instruction to measure biological information after attaching the biological information measuring device onto the wrist.

Then, as shown in FIG. 8H, the user presses the blood pressure measurement switch 52B to start blood pressure measurement.

In this example, the body 10 has a release button 19 (see FIGS. 1A, 2, and 5) as an unlocking mechanism for releasing the sticking and/or engagement between the protrusion 31 serving as the first locking element and the magnet 33 serving as the second locking element. As shown in FIG. 5, the release button 19 is integrally formed with a slide plate 19a. When this release button 19 is pushed into the body 10, the slide plate 19a is inserted like a wedge between the one end part d of the first plate frame member 30a and the other end part h of the second plate frame member 30b shown in FIG. 6B to release the sticking and/or engagement between the protrusion 31 and the magnet 33.

Although a convex shape is used as the first fixing element and a concave shape is used as the second fixing element in the above example, the present invention is not limited to this. For example, a concave shape may be used as the first fixing element and a convex shape may be used as the second fixing element. Even in this case, the same effects can be obtained.

In the above example, the user finds the length of the ring of the belt length guide member 200 that exactly matches the circumference of the wrist 90 by using the belt length guide member 200 (FIGS. 7A and 7B) before attachment. However, this is not restrictive. The user may use the marks M provided on the outer surface of the front end part b of the belt 20. In this case, the user checks and remembers a number of a mark M that exactly matches the circumference of the wrist 90.

(Internal Structure of Device)

Figure 9:
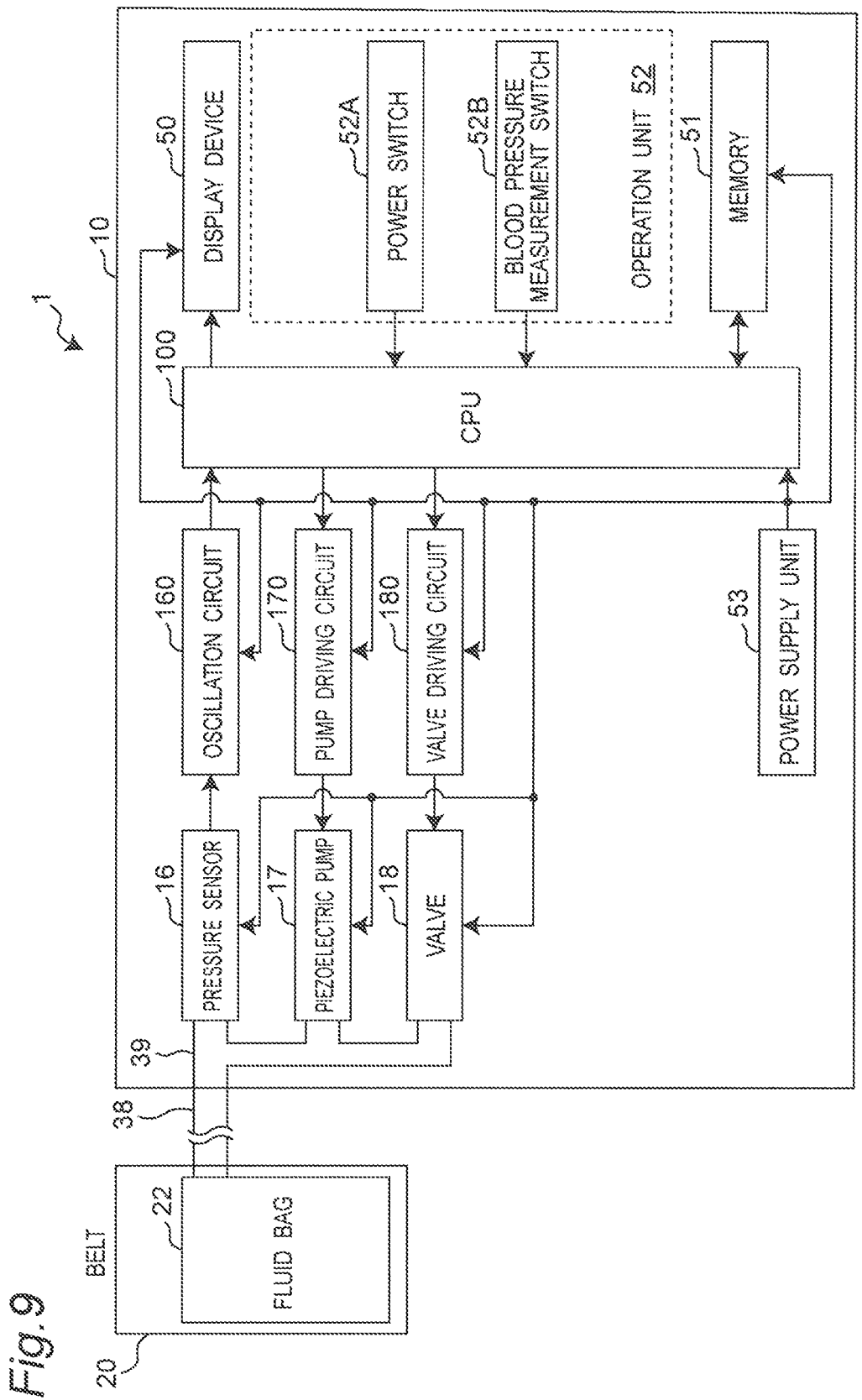
FIG. 9 is a block diagram schematically showing a configuration of a control system inside the biological information measuring device.

FIG. 9 schematically shows an internal configuration of a control system of the biological information measuring device 1. Mounted in the body 10 in addition to the display device 50 and the operation unit 52 are a CPU (Central Processing Unit) 100, a memory 51, a power supply unit 53, a piezoresistive pressure sensor 16, a piezoelectric pump (hereinafter referred to as "pump") 17 that supplies air as a fluid to the fluid bag 22, a valve 18 for adjusting pressure (back pressure) on a discharge side of the pump 17, an oscillation circuit 160 that converts output from the pressure sensor 16 into a frequency, a pump driving circuit 170 that drives the pump 17, and a valve driving circuit 180 that drives the valve 18. The pressure sensor 16, the pump 17, and the valve 18 are connected to the fluid bag 22 contained in the belt 20 through an air pipe 39 provided inside the body and a nipple 38 (see FIG. 5) that is fitted and communicated with the air pipe 39. As a result, air as a fluid flows between the fluid bag 22 and each of the pressure sensor 16, the pump 17, and the valve 18.

The display device 50 includes a display, an indicator, and the like, and displays predetermined information according to a control signal from the CPU 100.

In the operation unit 52, the power switch 52A receives an instruction to turn on/off the power supply unit 53. The blood pressure measurement switch 52B receives an instruction to start blood pressure measurement and an instruction to display data of a measurement result of a blood pressure value stored in the memory 51 on the display device 50. These switches 52A and 52B supply an operation signal based on an instruction from a user to the CPU 100.

The memory 51 stores therein a program for controlling the biological information measuring device 1, setting data for setting various functions of the biological information measuring device 1, and data of measurement results of blood pressure values. Furthermore, the memory 51 is used as a work memory or the like when a program is executed.

The power supply unit 53 supplies electric power to each of the CPU 100, the pressure sensor 16, the pump 17, the valve 18, the display device 50, the memory 51, the oscillation circuit 160, the pump driving circuit 170, and the valve driving circuit 180.

The oscillation circuit 160 oscillates based on an electric signal value that is based on a change in electric resistance due to a piezoresistive effect from the pressure sensor 16 and supplies a frequency signal having a frequency according to the electric signal value of the pressure sensor 16 to the CPU 100.

The CPU 100 operates as a pressure control unit according to the program for controlling the biological information measuring device 1 stored in the memory 51. The CPU 100 causes the pump drive circuit 170 to drive the pump 17 according to an operation signal from the operation unit 52 and controls the valve drive circuit 180 to drive the valve 18. The valve 18 is opened or closed to discharge or enclose air from or in the fluid bag 22 and thus controls the back pressure. Furthermore, the CPU 100 calculates a blood pressure value based on a signal from the pressure sensor 16 and controls the display device 50 and the memory 51.

The pump 17 supplies air as a fluid to the fluid bag 22 in order to increase the pressure (cuff pressure Pc) in the fluid bag 22 contained in the belt 20. The valve 18 is opened or closed to discharge or enclose air in the fluid bag 22 and thus controls the cuff pressure Pc. The pump driving circuit 170 drives the pump 17 based on a control signal given from the CPU 100. The valve driving circuit 180 opens and closes the valve 18 based on a control signal given from the CPU 100.

The pressure sensor 16 and the oscillation circuit 160 operate as a pressure detection unit that detects the cuff pressure Pc. The pressure sensor 16 is, for example, a piezoresistive pressure sensor and is connected to the pump 17, the valve 18, and the fluid bag 22 contained in the belt 20 through the air pipe 39. In this example, the oscillation circuit 160 oscillates based on an electric signal value that is based on a change in electric resistance due to the piezoresistive effect from the pressure sensor 16 and supplies a frequency signal having a frequency according to the electric signal value of the pressure sensor 16 to the CPU 100.

(Operation of Blood Pressure Measurement)

Operation of the biological information measuring device 1 configured as above will be described below.

Figure 10:
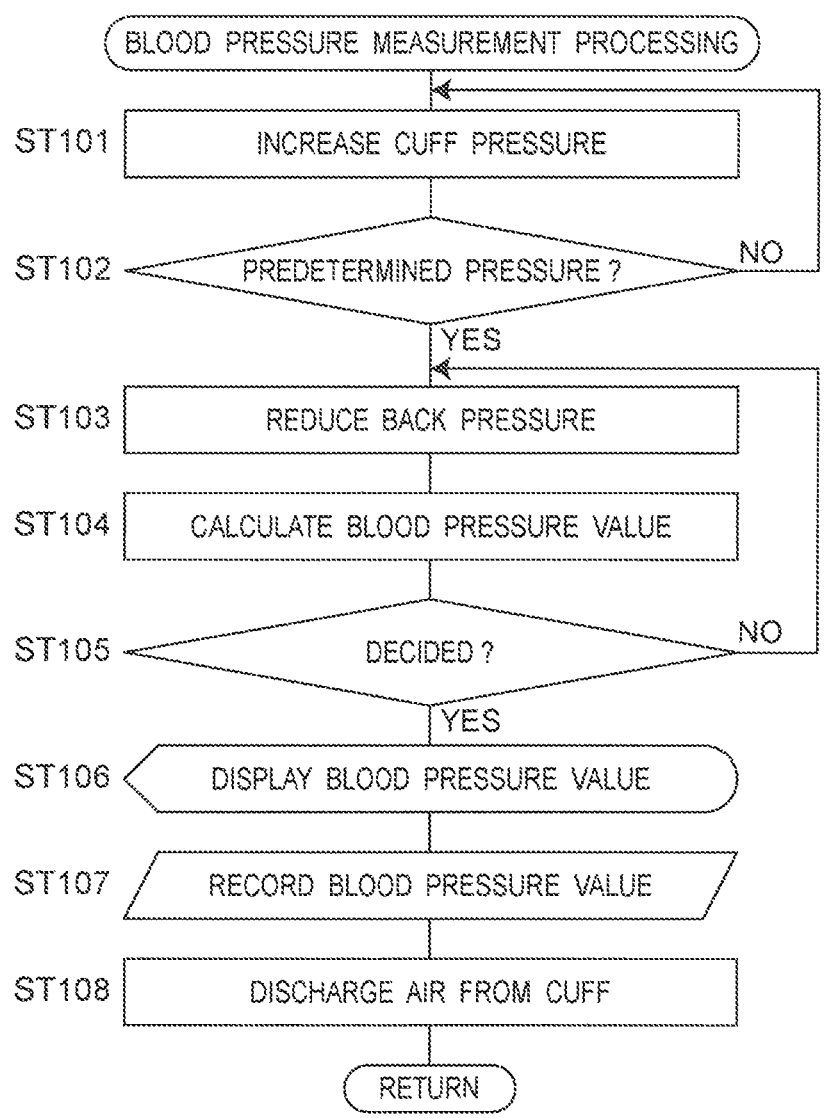
FIG. 10 is a flowchart showing blood pressure measurement processing executed by the biological information measuring device.

FIG. 10 is a flowchart showing blood pressure measurement processing executed by the biological information measuring device 1. In a case where blood pressure is measured according to a general oscillometric method, the following operations are generally performed. That is, a cuff is wrapped around a portion to be measured (such as a wrist) of a user in advance. During measurement, the pump and the valve are controlled to increase the cuff pressure Pc to pressure higher than systolic blood pressure and then gradually reduce the pressure. In the process of reducing the pressure, the cuff pressure Pc is detected by the pressure sensor, and a fluctuation in arterial volume generated in an artery in the portion to be measured is extracted as a pulse wave signal. Based on changes (mainly rising and falling) in amplitude of the pulse wave signal accompanying changes in the cuff pressure Pc at that time, systolic blood pressure and diastolic blood pressure are calculated.

In this biological information measuring device 1, the CPU 100 measures a blood pressure value of a user by the oscillometric method according to the flow of FIG. 10.

Specifically, when the blood pressure measurement switch 52B is pressed while the power switch 52A is on, the biological information measuring device 1 starts blood pressure measurement, as shown in FIG. 10. To start blood pressure measurement, the CPU 100 initializes a processing memory area and supplies a control signal to the valve driving circuit 180. The valve driving circuit 180 opens the valve 18 to discharge the air in the fluid bag 22 of the belt 20 based on the control signal. Then, control for adjusting 0 mmHg of the pressure sensor 16 is performed.

In FIG. 10, when blood pressure measurement starts, the CPU 100 first causes the valve drive circuit 180 to close the valve 18 and then causes the pump drive circuit 170 to drive the pump 17. In this way, the CPU 100 performs pressurizing processing for sending air to the fluid bag 22. This expands the fluid bag 22 and gradually increases the cuff pressure Pc (step ST101).

When the cuff pressure Pc is increased to reach a predetermined pressure (YES in step ST102), the CPU 100 causes the pump drive circuit 170 to stop the pump 17 and then causes the valve drive circuit 180 to gradually open the valve 18. This contracts the fluid bag 22 and gradually reduces the cuff pressure Pc (step ST103).

The predetermined pressure is a pressure (e.g., systolic blood pressure+30 mmHg) sufficiently higher than the systolic blood pressure of the user. The predetermined pressure is stored in the memory 51 in advance or is decided based on systolic blood pressure estimated according to a predetermined calculation formula by the CPU 100 during the pressurization of the cuff pressure Pc (see, for example, Japanese Patent Laid-Open No. 2001-70263).

As for a depressurization rate, a target depressurization rate is set during the pressurization of the cuff, and the CPU 100 controls an opening degree of the valve 18 so that the depressurization rate becomes the target depressurization rate (see Japanese Patent Laid-Open No. 2001-70263).

In the process of reducing the pressure, the pressure sensor 16 detects the cuff pressure Pc via the belt 20. Based on the cuff pressure Pc, the CPU 100 calculates a blood pressure value (systolic blood pressure and diastolic blood pressure) by applying an algorithm described later according to the oscillometric method (step ST104). A blood pressure value may be calculated not only in the depressurizing process but also in the pressurizing process.

When the blood pressure value is calculated and is then decided (YES in step ST105), the CPU 100 displays the calculated blood pressure value on the display device 50 (step ST106) and stores the blood pressure value in the memory 51 (step ST107).

Next, the CPU 100 causes the valve drive circuit 180 to open the valve 18 so that the air in the fluid bag 22 of the belt 20 is discharged (step ST108).

Then, when the power switch 52A is pressed, the blood pressure measurement ends.

This biological information measuring device 1 is attached to the wrist 90 to be measured in a state where the base end part a of the belt 20 and the front end part b of the belt 20 overlap each other by the buckle 30, as shown in FIG. 4. Therefore, a degree of expansion of the fluid bag 22 on the back side of the hand, that is, expansion of the fluid bag 22 in the thickness direction increases. This makes it possible to accurately detect a pulse wave. Accordingly, the blood pressure measurement accuracy is improved. Furthermore, the front end part b of the belt 20 does not protrude in the fastened state. This improves appearance.

The biological information measuring device 1 may measure various kinds of biological information such as a pulse value, an activity amount, a blood oxygen concentration value other than the blood pressure value.

To remove this biological information measuring device 1 from the wrist 90, the user opens the first plate frame member 30a and the second plate frame member 30b of the buckle 30 and pulls out the wrist 90 from the belt 20 while keeping the ring of the belt 20 large.

In the second and subsequent attachment, the user only needs to pass the wrist 90 through the ring of the belt 20 in a state where the first plate frame member 30a and the second plate frame member 30b of the buckle 30 are open and then close the buckle 30. Therefore, the user can easily attach the biological information measuring device 1 onto the wrist 90.

Even if the other end part h of the second plate frame member 30b is displaced from the adjusted position with respect to the front end part b of the belt 20, the marks M are provided on the outer surface of the front end part b of the belt 20 in the biological information measuring device 1. This allows the user to attach the other end part h of the second plate frame member 30b to the original attachment position (adjusted position) of the front end part b of the belt 20 with reference to the marks M.

Furthermore, the marks M are provided on the bottom of the groove 26 having a concave cross section formed on the outer surface of the front end part b of the belt 20. This can avoid a situation where the marks M are peeled off, for example, even if the outer surface of the belt 20 comes into contact with the outside as a result of use of the biological information measuring device 1.

As described above, a biological information measuring device of the present disclosure wound around a rod-shaped portion to be measured, comprises:
 a band-shaped belt that is wound around the portion to be measured;
 a body that is disposed on a base end part of the belt in a longitudinal direction and is provided with an element for measuring biological information; and
 a buckle that connects the base end part and a front end part on an opposite side in the longitudinal direction of the belt so that the belt becomes annular,
 wherein
 the buckle includes
  a first plate frame member that is attached at one end part thereof on an inner surface of the base end part of the belt so as to be rotatable about an axis that intersects the longitudinal direction of the belt, the first plate frame member extending in a plate shape from the one end part to an other end part on an opposite side,
  a second plate frame member that is attached at one end part thereof to the other end part of the first plate frame member so as to be rotatable about an axis parallel with the axis, the second plate frame member extending in a plate shape from the one end part to an other end part on an opposite side, and the other end part of the second plate frame member being attachable to the front end part of the belt, and
  a first plate part having a plate shape and being fixed to the other end part of the second plate frame member so as to be integral with the second plate frame member and a second plate part having a plate shape and attached so as to be rotatable about a rotation axis parallel with the axis and located at a forefront end of the other end part,
 the second plate part has a sticking-out part that extends beyond the first plate part toward the one end part of the second plate frame member when the second plate member overlaps an outer surface of the first plate part,
 a first fixing element is provided on a side of the sticking-out part that becomes an inner surface when the second plate part overlaps the outer surface of the first plate part, and a second fixing element that is engageable with the first fixing element is provided on an outer surface of the front end part of the belt, and
 a first engagement protrusion is provided on a specific part of an end side of the first plate part closer to the one end part of the second plate frame member, and a second engagement protrusion that overlaps the first engagement protrusion in a thickness direction and is engageable with the first engagement protrusion is provided in a part of the second plate part that corresponds to the first engagement protrusion.

In the present specification, a "base end part", a "front end part", a "one end part" and an "other end part" are not limited to a base end, a front end, one end, and the other end, respectively, and may refer to a part in a certain range. Meanwhile, a "foremost end" substantially refers to a front end.

An "inner surface" refers to a surface that faces a portion to be measured in a state where the biological information measuring device is wound around the portion to be measured. An "outer surface" refers to a surface opposite to the inner surface in a state where the biological information measuring device is wound around the portion to be measured.

"Biological information" broadly encompasses a blood pressure value, a pulse value, an activity amount, a blood oxygen concentration value, and the like.

The biological information measuring device of the present disclosure includes a band-shaped belt to be wound around the portion to be measured, a body that is disposed on a base end part in a longitudinal direction of the belt and is provided with an element for measuring biological information, and a buckle that connects the base end part and a front end part on the opposite side in the longitudinal direction of the belt so that the belt becomes annular. Furthermore, the buckle includes a second plate frame member attachable to the front end part of the belt and a first plate frame member connected to the second plate frame member and the body.

When attaching this biological information measuring device on the wrist, a user attaches the biological information measuring device, for example, through the following attachment procedures (a) to (c).

(a) First, in a state where the body and the first plate frame member and the second plate frame member of the buckle 30 are open to each other, the user makes the second plate part open with respect to the first plate part (so that the second plate part does not overlap the first plate part). At the same time, the front end part of the belt is arranged along the inner surface of the second plate frame member. In this state, the other end part of the second plate frame member and the front end part of the belt are not fixed to each other. Therefore, the user can slide the front end part of the belt in the longitudinal direction along the inner surface of the second plate frame member and therefore can easily perform position adjustment between the other end part of the second plate frame member and the front end part of the belt. Thereby, the length of the ring of the belt can be variably set so as to exactly match the circumference of the portion to be measured.

(b) When the user finishes the position adjustment between the other end part of the second plate frame member and the front end part of the belt, the user then closes the second plate part with respect to the first plate part by rotating the second plate part about the rotary shaft. This causes the first fixing element provided on the side of the sticking-out part that becomes the inner surface to be engaged with the second fixing element provided on the outer surface of the front end part of the belt. As a result, the other end part of the second plate frame member is attached to the front end part of the belt. In this state, a first engagement protrusion provided in a specific part of an end side of the first plate part closer to the one end part of the second plate frame member and a second engagement protrusion provided in a part of the second plate part that corresponds to the first engagement protrusion overlap in a thickness direction and are engaged with each other. This keeps engagement between the other end part of the second plate frame member and the front end part of the belt while preventing the second plate part from being opened carelessly with respect to the first plate part. As a result, displacement between the other end part of the second plate frame member and the front end part of the belt is prevented.

(c) Then, the user puts his or her hand through the ring of the belt in a state where the belt is annular and the body and the first plate frame member and the second plate frame member of the buckle are opened to each other and then folds the body and the first plate frame member and the second plate frame member of the buckle on each other. This allows the user to easily attach the biological information measuring device to the wrist.

In the biological information measuring device of one embodiment, a groove having a concave cross section for avoiding interference with the first and second engagement protrusions is provided in a part corresponding to the first and second engagement protrusions in a width direction of the belt on the outer surface of the belt so as to extend along the longitudinal direction.

In the biological information measuring device according to this embodiment, the groove having the concave cross section avoids interference between the outer surface of the belt and the first and second engagement protrusions. As a result, a thickness of a part of the biological information measuring device where the body, the buckle, and the belt overlap each other can be reduced as a whole.

In the biological information measuring device of one embodiment, marks for adjusting a position of the front end part of the belt are provided on a bottom of the groove on the outer surface of the belt.

In the biological information measuring device according to this embodiment, the user can perform position adjustment with reference to the marks for position adjustment when performing position adjustment (the attachment procedure (a)) between the other end part of the second plate frame member and the front end part of the belt by sliding the front end part of the belt in the longitudinal direction along the inner surface of the first plate part. This makes it possible to perform position adjustment accurately and with good reproducibility. The marks are provided on the bottom of the groove having a concave cross section provided on the outer surface of the front end part of the belt. This can avoid a situation where the marks are peeled off even if the outer surface of the belt comes into contact with the outside as a result of use of the biological information measuring device.

In the biological information measuring device of one embodiment, an operation protrusion for rotating the second plate part about the rotation axis is provided on a foremost end of the sticking-out part.

In the biological information measuring device according to this embodiment, the user can easily rotate the second plate part about the rotation axis by hooking his or her finger on the operation protrusion provided on the foremost end of the sticking-out part.

In the biological information measuring device of one embodiment,
- a first lock element is provided on the outer surface of the first plate part, and a cutout or an opening is provided in a part of the second plate part that corresponds to the first lock element when the second plate part overlaps the outer surface of the first plate part,
- a second lock element is provided on an inner surface side of the base end part of the belt or the one end part of the first plate frame member, and
- the first lock element and the second lock element stick to each other and/or are engaged with each other through the cutout or the opening of the second plate part in an attachment state where the second plate part overlaps the outer surface of the first plate part and an inner surface of the body and the first plate frame member and the second plate frame member of the buckle are folded to overlap each other.

In the biological information measuring device according to this embodiment, the first lock element and the second lock element stick to each other and/or are engaged with each other through the cutout or the opening of the second plate part when the body and the first plate frame member and the second plate frame member of the buckle are folded on each other (the attachment procedure (c)). This prevents the buckle from being opened carelessly. An unlock mechanism for releasing the sticking and/or the engagement is desirably provided.

In the biological information measuring device of one embodiment, the second fixing element includes a plurality of second fixing elements arranged along the longitudinal direction of the belt so that an attachment position of the other end part of the second plate frame member becomes adjustable in the longitudinal direction of the belt.

In the biological information measuring device according to this embodiment, a plurality of the second fixing elements are arranged side by side along the longitudinal direction of the belt. This allows the user to select a second fixing element that exactly matches the first fixing element of the second plate part among the plurality of second fixing elements when performing position adjustment (the attachment procedure (a)) between the other end part of the second plate frame member and the front end part of the belt by sliding the front end part of the belt in the longitudinal direction along the inner surface of the first plate part. Thereby, the length of the ring of the belt can be variably set so as to exactly match the circumference of the portion to be measured.

In the biological information measuring device of one embodiment, a pair of hook parts that permit insertion of the front end part of the belt along the inner surface of the second plate frame member and regulates separation of the front end part of the belt from the inner surface of the second plate frame member are provided on respective sides, in a width direction, of the other end part of the second plate frame member.

In the biological information measuring device according to this embodiment, the pair of hook parts permit insertion of the front end part of the belt along the inner surface of the second plate frame member and regulates separation of the front end part of the belt from the inner surface of the second plate frame member when the user performs position adjustment (the attachment procedure (a)) between the other end part of the second plate frame member and the front end part of the belt by sliding the front end part of the belt in the longitudinal direction along the inner surface of the second plate frame member. As a result, the front end part of the belt slides smoothly without being separated from the inner surface of the second plate frame member. Therefore, the position adjustment can be easily performed.

The biological information measuring device according to the embodiment is desirably configured such that
the first plate frame member and the second plate frame member have a first opening and a second opening passing therethrough with respect to plate surfaces, respectively, and
the first opening of the first plate frame member and the second opening of the second plate frame member are communicated with each other in a thickness direction of the body in an attachment state where the second plate part overlaps the outer surface of the first plate part and the inner surface of the body and the first plate frame member and the second plate frame member of the buckle are folded so as to overlap each other.

In the biological information measuring device according to this embodiment, the first opening of the first plate frame member and the second opening of the second plate frame member are continuous with each other in the thickness direction of the body in the attachment state, and therefore a fluid bag for pressing the portion to be measured can be disposed on an inner side of the body. As a result, the portion to be measured located on the inner side of the body is pressed.

The above embodiment is an illustrative example, and various modifications can be made without departing from the scope of the present invention. The above embodiments may be independent of each other or may be combined with each other. Various features in different embodiments may be independent of each other or may be combined with each other.

The invention claimed is:

1. A biological information measuring device wound around a rod-shaped portion to be measured, comprising:
  a band-shaped belt that is wound around the portion to be measured;
  a body that is disposed on a base end part of the belt in a longitudinal direction and is provided with an element for measuring biological information; and
  a buckle that connects the base end part and a front end part on an opposite side in the longitudinal direction of the belt so that the belt becomes annular,
  wherein
  the buckle includes
    a first plate frame member that is attached at one end part thereof on an inner surface of the base end part of the belt so as to be rotatable about an axis that intersects the longitudinal direction of the belt, the first plate frame member extending in a plate shape from the one end part to an other end part on an opposite side,
    a second plate frame member that is attached at one end part thereof to the other end part of the first plate frame member so as to be rotatable about an axis parallel with the axis, the second plate frame member extending in a plate shape from the one end part to an other end part on an opposite side, and the other end part of the second plate frame member being attachable to the front end part of the belt, and
    a first plate part having a plate shape and being fixed to the other end part of the second plate frame member so as to be integral with the second plate frame member and a second plate part having a plate shape and attached so as to be rotatable about a rotation axis parallel with the axis and located at a forefront end of the other end part,
  the second plate part has a sticking-out part that extends beyond the first plate part toward the one end part of the second plate frame member when the second plate member overlaps an outer surface of the first plate part,
  a first fixing element is provided on a side of the sticking-out part that becomes an inner surface when the second plate part overlaps the outer surface of the first plate part, and a second fixing element that is engageable with the first fixing element is provided on an outer surface of the front end part of the belt, and
  a first engagement protrusion is provided on a specific part of an end side of the first plate part closer to the one end part of the second plate frame member, and a second engagement protrusion that overlaps the first engagement protrusion in a thickness direction and is engageable with the first engagement protrusion is provided in a part of the second plate part that corresponds to the first engagement protrusion.

2. The biological information measuring device according to claim 1, wherein a groove having a concave cross section for avoiding interference with the first and second engagement protrusions is provided in a part corresponding to the first and second engagement protrusions in a width direction of the belt on the outer surface of the belt so as to extend along the longitudinal direction.

3. The biological information measuring device according to claim 2, wherein marks for adjusting a position of the front end part of the belt are provided on a bottom of the groove on the outer surface of the belt.

4. The biological information measuring device according to claim 1, wherein an operation protrusion for rotating the second plate part about the rotation axis is provided on a foremost end of the sticking-out part.

5. The biological information measuring device according to claim 1, wherein
  a first lock element is provided on the outer surface of the first plate part, and a cutout or an opening is provided in a part of the second plate part that corresponds to the first lock element when the second plate part overlaps the outer surface of the first plate part, a second lock element is provided on an inner surface side of the base end part of the belt or the one end part of the first plate frame member, and the first lock element and the second lock element stick to each other and/or are engaged with each other through the cutout or the opening of the second plate part in an attachment state where the second plate part overlaps the outer surface of the first plate part and an inner surface of the body and the first plate frame member and the second plate frame member of the buckle are folded to overlap each other.

6. The biological information measuring device according to claim 1, wherein the second fixing element includes a plurality of second fixing elements arranged along the longitudinal direction of the belt so that an attachment position of the other end part of the second plate frame member becomes adjustable in the longitudinal direction of the belt.

7. The biological information measuring device according to claim 1, wherein a pair of hook parts that permit insertion of the front end part of the belt along the inner surface of the second plate frame member and regulates separation of the front end part of the belt from the inner surface of the second plate frame member are provided on respective sides, in a width direction, of the other end part of the second plate frame member.

* * * * *